United States Patent [19]
Krug et al.

[11] Patent Number: 5,490,218
[45] Date of Patent: * Feb. 6, 1996

[54] DEVICE AND METHOD FOR INSPECTION OF BAGGAGE AND OTHER OBJECTS

[75] Inventors: Kristoph D. Krug; Jay A. Stein, both of Framingham; Adam L. Taylor, Boston, all of Mass.

[73] Assignee: Vivid Technologies, Inc., Waltham, Mass.

[ * ] Notice: The portion of the term of this patent subsequent to Jun. 7, 2011, has been disclaimed.

[21] Appl. No.: 165,737

[22] Filed: Dec. 10, 1993

Related U.S. Application Data

[63] Continuation of Ser. No. 566,083, Aug. 10, 1990, Pat. No. 5,319,547.

[51] Int. Cl.$^6$ ................................................ G01N 23/02
[52] U.S. Cl. .......................... 382/100; 378/53; 378/57; 382/199
[58] Field of Search ..................... 364/413.23; 382/22, 382/100, 141–142, 199, 173, 257, 272; 250/390.04; 378/53, 54, 57, 83

[56] References Cited

U.S. PATENT DOCUMENTS

| | | | |
|---|---|---|---|
| Re. 28,544 | 9/1975 | Stein et al. | 378/146 |
| 3,678,278 | 7/1972 | Peil | 250/515.1 |
| 3,832,545 | 8/1974 | Bartko | 376/159 |
| 3,840,747 | 10/1974 | Macovski | 250/369 |
| 3,843,881 | 10/1974 | Barton et al. | 250/269.1 |
| 3,848,130 | 11/1974 | Macovski | 378/98.9 |
| 3,884,816 | 5/1975 | Krug et al. | 378/57 |
| 3,919,467 | 11/1975 | Peugeot | 378/98.2 |
| 3,924,064 | 12/1975 | Nomura et al. | 378/57 |
| 3,924,129 | 12/1975 | Lemay | 364/413.19 |
| 3,944,830 | 3/1976 | Dissing | 378/55 |
| 3,996,471 | 12/1976 | Fletcher | 378/53 |
| 4,020,346 | 4/1977 | Dennis | 378/57 |

(List continued on next page.)

OTHER PUBLICATIONS

Bisignani et al., "Automated X-Ray Bomb Detection Techniques", 8079 Electro Conference Record, vol. 4, Paper 18/3 (1979).

Stefanski et al., "An X-Ray Inspection System For Security Screening Application", Proceedings 1977 International Conference on Crime Countermeasures—Science and Engineering, Jul. 25–29, 1977, pp. 57–64.

Richard G. Cumings, "A Survey of X-Ray Technology and Available Systems for Parcel Inspection", Proceedings 1979 Carnahan Conference on Crime Countermeasures, May 16–18, 1979, pp. 117–122.

Lehmann et al., "Generalized Image Combinations in Dual KVE Digital Radiography" Medical Physics, vol. 8, No. 5, p. 659, Sep./Oct. 1981.

Sartoris et al., "Bone Mineral Density in the Femoral Neck", American Journal of Roentegenology, vol. 144, p. 605 (1985).

Gustafsson et al., "X–ray Spectrophotometry for Bone–Mineral Determinations", Medical and Biomedical Engineering, p. 113 (Jan. 1974).

The "Norland Dichromatic Bone Densitometer" pamphlet, date unknown.

(List continued on next page.)

Primary Examiner—David M. Huntley
Attorney, Agent, or Firm—Fish & Richardson

[57] ABSTRACT

A device and method is provided for finding a specific material superimposed on an unknown background when the locations of the specific material and the background are unknown, for example, inside an item of baggage. The invention comprises exposing an area of an item to be inspected to x-rays of two substanitally different energies, making effective use of the characteristic material specific differences in photoelectric effect scattering and Compton scattering, and comparing the pairwise differential attenuation of the x-rays at nearby exposed subareas to determine whether differences in attenuation can be attributed to the presence of different amounts of the specific material overlying the respective subareas. The most probable subareas are indicated on a standard image on a monitor as being the most likely location of the overlying specific material.

73 Claims, 20 Drawing Sheets

U.S. PATENT DOCUMENTS

| | | | |
|---|---|---|---|
| 4,029,963 | 6/1977 | Alvarez et al. | 250/360 |
| 4,047,035 | 9/1977 | Dennhoven et al. | 378/57 |
| 4,070,581 | 1/1978 | Gibbons et al. | 250/455 T |
| 4,075,492 | 2/1978 | Boyd et al. | 378/7 |
| 4,138,721 | 2/1979 | Boyd | 378/14 |
| 4,139,771 | 2/1979 | Dennhoven et al. | 378/57 |
| 4,210,811 | 7/1980 | Dennhoven et al. | 378/57 |
| 4,216,499 | 8/1980 | Kunze et al. | 378/98.2 |
| 4,247,774 | 1/1981 | Brooks | 250/367 |
| 4,255,664 | 3/1981 | Rutt et al. | 378/5 |
| 4,366,382 | 12/1982 | Kotowski | 378/57 |
| 4,454,605 | 6/1984 | DeLucia | 378/57 |
| 4,463,375 | 7/1984 | Macovski | 378/98.12 |
| 4,530,006 | 7/1985 | Blaustein et al. | 378/98.8 |
| 4,539,648 | 9/1985 | Schatzki | 364/555 |
| 4,549,307 | 10/1985 | Macovski | 378/145 |
| 4,566,113 | 1/1986 | Donges et al. | 378/57 |
| 4,578,803 | 3/1986 | Macovski | 378/62 |
| 4,639,943 | 1/1987 | Heinze et al. | 378/96 |
| 4,641,331 | 2/1987 | Makino et al. | 378/108 |
| 4,644,578 | 2/1987 | Paolini | 378/146 |
| 4,686,695 | 8/1987 | Macovski | 378/146 |
| 4,736,401 | 4/1988 | Donges et al. | 378/146 |
| 4,748,649 | 5/1988 | Griesmer et al. | 378/97 |
| 4,756,015 | 7/1988 | Doenges et al. | 378/57 |
| 4,759,047 | 7/1988 | Donges et al. | 378/57 |
| 4,783,794 | 11/1988 | Dietrich | 378/57 |
| 4,788,705 | 11/1988 | Donges et al. | 378/121 |
| 4,817,121 | 3/1989 | Shimizu et al. | 378/57 |
| 4,827,528 | 5/1989 | Macovski | 382/263 |
| 4,841,554 | 6/1989 | Doenges et al. | 378/57 |
| 4,851,984 | 7/1989 | Doi et al. | 364/413.23 |
| 4,864,142 | 9/1989 | Gomberg | 250/390.04 |
| 4,870,670 | 9/1989 | Geus | 378/87 |
| 4,879,735 | 11/1989 | Owens | 378/57 |
| 4,884,289 | 11/1989 | Glockmann et al. | 378/57 |
| 4,980,923 | 12/1990 | Kawamoto et al. | 382/41 |
| 4,987,584 | 1/1991 | Doenges | 378/100 |
| 5,016,173 | 5/1991 | Kenet et al. | 382/128 |
| 5,022,062 | 6/1991 | Annis | 378/86 |
| 5,031,226 | 7/1991 | DeLange | 382/199 |
| 5,044,002 | 8/1991 | Stein | 378/54 |
| 5,133,020 | 7/1992 | Giger et al. | 382/6 |
| 5,182,764 | 1/1993 | Peschmann et al. | 378/57 |
| 5,253,283 | 10/1993 | Annis | 378/100 |

U.S. PATENT DOCUMENTS

Boston Globe article, "U.S. Says American Airlines Has Poor Security Record", dated Feb. 18, 1989.

Alvarez et al., "Characterization of the X–Ray Attenuation Properties of Explosives and Their Implications in Baggage Screening", Report No. FAA–RD–79–50, Mar. 1979.

EG&G Astrophysics brochures, dates unknown.

Scan–tech Security brochure, date unknown.

Heimann Systems Co. brochures, 1989.

Cann, "A Clinicians Guide to the Use of Bone Mass Measurements", p. 12, date unknown.

Wehner et al., "Non–Invasive Bone Mineral Measurements", Seminars in Nuclear Medicine, vol. XIII, No. 3, p. 282, Jul. 1983.

Dunn et al., "Measurement of Bone Mineral Content in Human Vertebrae and Hip by Dual Proton Absorptiometry", Radiology, vol. 136, No. 2, p. 485 (Aug. 1980).

A. L. Hall et al., "Experimental system for dual energy scanned projection radiography" SPIE, vol. 314 Digital Radiography (1981) pp. 155–159.

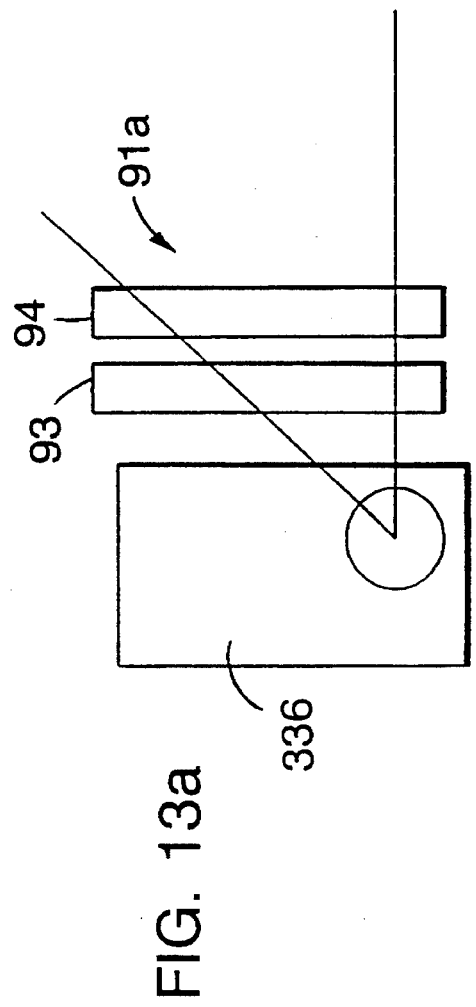
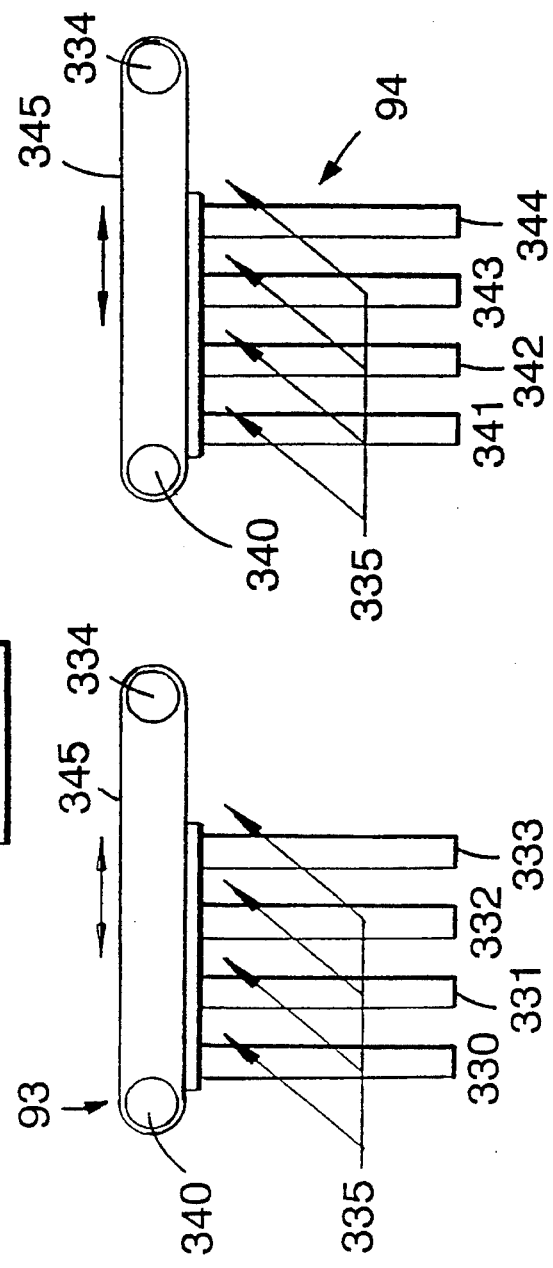

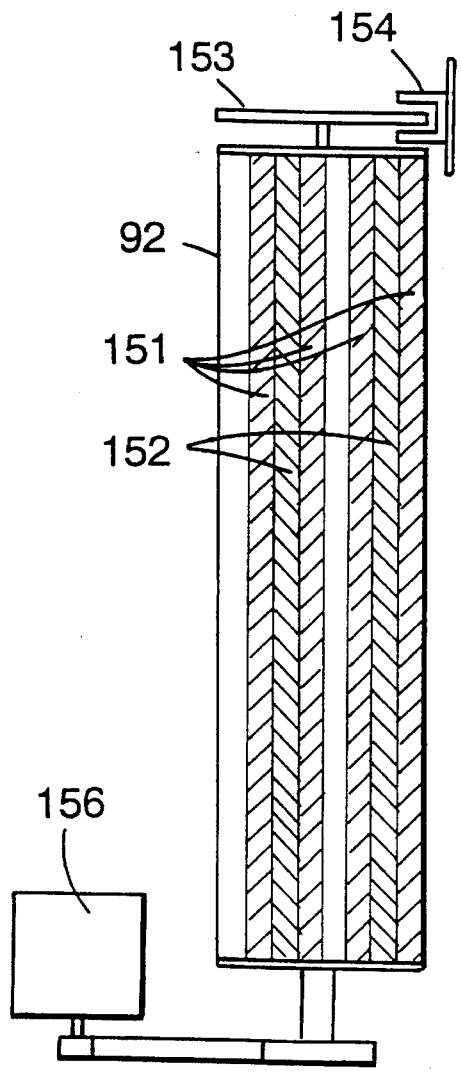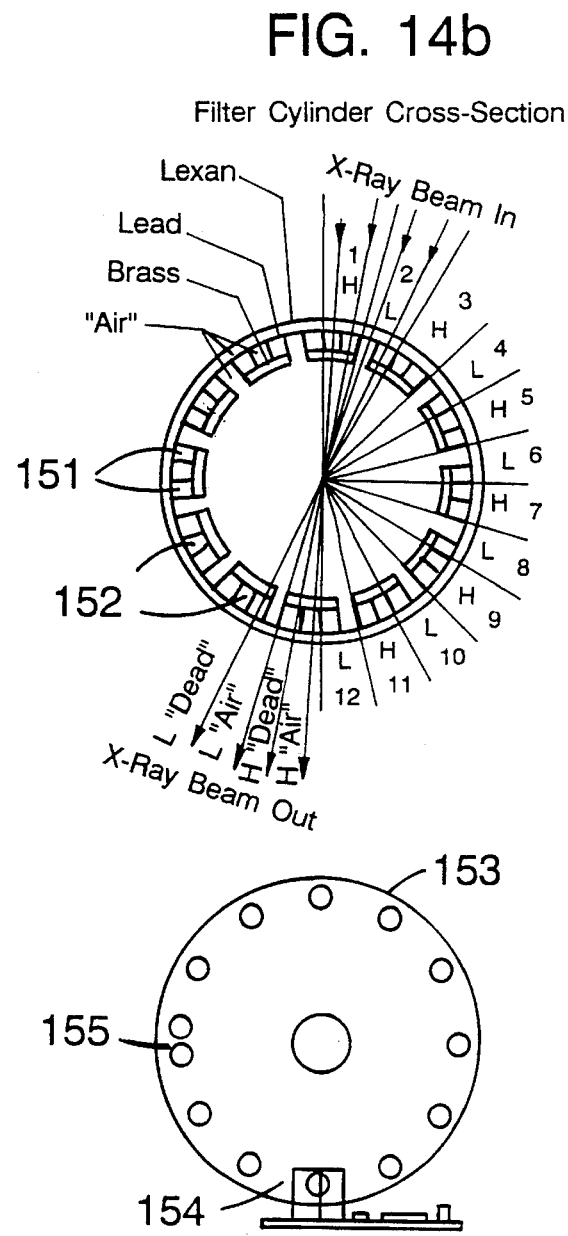
FIG. 14b
FIG. 14a
FIG. 14c

DEVICE AND METHOD FOR INSPECTION OF BAGGAGE AND OTHER OBJECTS

This is a continuation of application Ser. No. 07/566,083, filed Aug. 10, 1990, now U.S. Pat. No. 5,319,547.

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

BACKGROUND OF THE INVENTION

The present invention relates to a method which utilizes at least two energy bands of x-rays to inspect objects subject to x-ray inspection (e.g., baggage) for a specific substance which can be characterized by a specific composite atomic number 'Z'.

It is known to inspect objects using single energy x-rays to present an image of the objects with shading representing varying degrees of mass density (opaqueness to x-rays).

It is known to inspect objects using a dual-energy x-ray system and to present an image with color proportional to the ratio of one energy band to the other on a pixel by pixel basis.

Such x-ray inspection systems incorporate an x-ray single or dual energy source, a conveyor, slider, or scanning system to scan the object to be inspected with the x-ray beam, a detector or array of detectors that convert the x-ray flux which penetrates the object to be inspected into pixels of values which represent the x-ray image(s) resulting from the scan, a computing element which may optionally filter, average, enhance, contrast adjust, or otherwise process the image of values output from the detector system, and a display system which presents a black and white or color display of the resulting image of pixel values.

It is known to employ a dual energy x-ray inspection system and to use the value of the ratio of one energy band's attenuation values to the other to discriminate between low-Z material (plastics) and high-Z materials (metals) and to display the respective values as a color difference in the displayed image. These systems display the resulting high-Z to low-Z color-encoded image based on the value of the ratio of the attenuation values at the high and low bands of x-rays for each pixel at a time repeated for every pixel in the image. This method is unable to distinguish composite materials such as metal over plastic and in these cases, an intermediate color is displayed.

The discrimination ability of these systems is insufficient to discriminate adequately between different types of plastics or plastic-like materials, and in the presence of overlying materials, is unable to accurately indicate the presence of specific plastics or metals.

SUMMARY OF THE INVENTION

Our invention features, in general, a device and method of operation for detecting a specific material that may be present in an ensemble of objects. The device includes means to expose an area of the ensemble to x-ray energies to produce dual energy image information of the ensemble. The device further includes means to computer-process such dual energy information to detect the specific material on the basis of comparisons of selected subareas of the exposed area to other subareas in the vicinity of the selected subareas.

In one important aspect, our invention features, in general, a device and method of operation for detecting a bomb that may be present in a container of objects. The device includes means to expose an area of the container to x-ray energies to produce dual energy information of the container and its contents. The device further includes means to computer-process such dual energy information to detect the bomb on the basis of comparisons of selected subareas of the exposed area to other subareas in the vicinity of the selected subareas.

Our invention features a device and method of operation for detecting a specific material that may be present in an ensemble of objects comprising means to expose an area of the ensemble to x-rays of at least two substantially different energy bands to produce dual energy image information of the ensemble. The device further includes means to computer-process such dual energy information to detect the specific material on the basis of comparisons between attenuation image information from at least one of the energy bands and positionally corresponding image information of parameter P values derived from correlations of the dual energy image information with values in a predetermined lookup table reflecting attenuation at high and low energy bands over a range of thicknesses of a selected specific material and a range of thicknesses of a representative overlay material, with attenuation of a constant thickness of the overlay material and varying thicknesses of the specific material represented by the parameter P.

In preferred embodiments, the means to computer-process includes means for evaluating gradients of values in at least one of the images and/or means for evaluating gradients of values in both the attenuation image and the image of P values. The device provides means for selecting the regions of the attenuation image information for the comparisons on the basis of the steepness of gradients of attenuation values in the attenuation image. The above devices further provide means for selecting which employs an edge finding operator. The device also includes means for generating gradient values $H_s$ for substantially all subareas and means for pruning to remove subareas with $H_s$ values below a selected threshold, and means for thereafter performing the comparisons using the remaining $H_s$ values.

Another feature of our invention is a device and method of operation for detecting and indicating the probable presence of a specific material in an ensemble of objects, comprising means for exposing the item to x-rays of at least two substantially different energy levels, means for generating for each subarea over the exposed area a set of data values representing logarithms of x-ray attenuation at the subarea at each of the energy levels, means for processing the data for the subarea to compute the values of (H,L) for the subarea, wherein H is the logarithm of the attenuation of the x-rays at the subarea at the higher energy level and L is the logarithm of the attenuation of the x-rays at the subarea at the lower energy level, and means for applying an edge finding or gradient evaluating operator such as a Sobel operator to image data of at least one energy level, means for generating gradient values $H_s$ for substantially all subareas, means for pruning to remove subareas with gradient values $H_s$ below a selected gradient threshold, means for determining for remaining subareas with gradient values $H_s$ above the selected gradient threshold parameter P values using a lookup table in computer storage reflecting x-ray attenuation at high and low energy bands over a range of thicknesses of the selected specific material and a range of thicknesses of a representative overlay material, with attenuation of a constant thickness of the overlay material and varying thicknesses of the specific material represented by the parameter P, means for applying the gradient evaluating operator to P image data formed using the parameter P values for the remaining subareas, means for generating gradient values $P_s$ for the remaining subareas, means for calculating a ratio $H_s/P_s$ for the remaining subareas, means for raising the ratio to a power at least as large as unity to emphasize large values of the ratio, and means for storing the ratio $H_s/P_s$ raised to the power for substantially all of the remaining subareas. The device further comprises means for selecting an alarm threshold on the ratio $H_s/P_s$ raised to the power so that subareas having the ratio $H_s/P_s$ raised to the power above the alarm threshold are strongly indicative of presence of the specific material, means for applying a dilation algorithm using the H values and the L values for the image data, means for sounding an alarm if a certain number of subarea values are above the alarm threshold, means for applying an erosion algorithm to eliminate spurious noise in the image data, and means for displaying the image data with areas of particular interest highlighted.

A feature of the invention is a device and method of operation for inspecting an ensemble of physical objects. The device comprises means to expose an area of the ensemble to x-rays of at least two substantially different energy bands and detection means responsive to the x-rays passing through the ensemble to generate for subareas over the exposed area respective sets of values representing the attenuation of the x-rays at each of the energy bands. Comparison means are employed, operative on differences in attenuation between subareas in a neighborhood to determine the presence of a specific material in the neighborhood, and indicating means are provided responsive to the comparisons, for indicating the presence of the specific material in the ensemble.

Preferably the indicating means of the device is a visual display of an x-ray image and the indication is of the form of distinguished subareas at which the specific material is probably present.

Preferably the comparison means of the device includes a lookup table reflecting attenuation at high and low energy bands over a range of thicknesses of a selected specific material and a range of thicknesses of a representative overlay material. Attenuation of a constant thickness of the overlay material and varying thicknesses of the specific material is represented by a parameter P. The device includes means to reference actual attenuation measurements of subareas at an energy band with parameter P values for said subareas, and using the determination in determining the presence of the specific material.

Various preferred embodiments have one or more of the following features. The comparison means of the device include means to combine, according to a predetermined formula, values representing the attenuation of the x-rays for subareas in the neighborhood to provide an attenuation measure that reflects the difference in the attenuation qualities between the subareas and means to compare the measure to a reference related to the specific material or materials for which the inspection is conducted. Preferably, the values generated by the device representing the attenuation of the x-rays at the energy bands are logarithms of x-ray attenuation at each of the energy bands at each subarea.

In preferred embodiments, the comparison means of the device comprises means for computing for a selected test subarea of the exposed area the values $(H_T,L_T)$ wherein $H_T$ is the logarithm of the attenuation of the x-rays at the higher energy band at the test subarea and $L_T$ is the logarithm of the attenuation of the x-rays at the lower energy band at the test subarea, and means for computing for a subarea nearby the test subarea the values $(H_B,L_B)$ wherein $H_B$ is the logarithm of the attenuation of the x-rays at the higher energy band at the nearby subarea and $L_B$ is the logarithm of the attenuation of the x-rays at the lower energy band at the nearby subarea. The comparison means are constructed to employ the values $(H_T,L_T)$ and $(H_B,L_B)$ in determining the presence of the specific material or materials.

Preferably the device further comprises means for providing p-values P representing attenuation characteristics of various overlying materials, means for associating a p-value $P_T$ with the values $(H_T,L_T)$ with the p-value $P_T$ proportional to the thickness of overlying materials at the test subarea, and means for associating a p-value $P_B$ with the values $(H_B,L_B)$ with the p-value $P_B$ proportional to the thickness of overlying materials at the nearby subarea. The device further includes means for computing the value of $|(H_T-H_B)/(P_T-P_B)|=\Delta H/\Delta P$ and means for associating $\Delta H/\Delta P$ with a relative probability measure for the presence of the specific material at respective subareas. In some embodiments, the relative probability measure is proportional to $(\Delta H/\Delta P)^q$, with q being a value chosen to emphasize extrema of the value of $\Delta H/\Delta P$. In particular embodiments, q=2. Preferably in these devices the means for associating a p-value P with the values (H,L) involves identifying the values with respective points from a set of points previously generated by numerically varying thicknesses of the specific material and the overlying materials.

Furthermore, in various embodiments, the device features means for computing the value of $(H_T-H_B)/(L_T-L_B)=K_{TB}$ and means for comparing the value of $K_{TB}$ with the value of $K_{MAT}$ wherein $K_{MAT}$ is an attenuation characteristic of a specific material for which the inspection is being conducted. In one such embodiment $K_{MAT}$ is a stored value developed by prior measurements and in another such embodiment $K_{MAT} \cong \mu_H/\mu_L$ determined by calculations wherein $\mu_H$ is the attenuation coefficient of the specific material exposed to the higher energy band x-rays and $\mu_L$ is the attenuation coefficient of the specific material exposed to the lower energy band x-rays.

In preferred embodiments, the device further comprises means for exposing selected numbers of samples of various known materials each of a range of different thicknesses to the x-rays of the different energy bands to measure the attenuation characteristic of the exposed samples to provide a reference for the comparison means. Certain embodiments further feature calculation means for interpolating between the measured values to estimate intermediate values for use in making the comparison.

In preferred embodiments, the device further comprises means for assigning to subareas, over the exposed area of the object, relative probabilities for the presence of the specific material based upon the comparisons, the indicating means being responsive to these relative probability assignments for indicating presence of the specific material in the object.

Our invention also features a baggage inspection device for detecting and indicating the probable presence of a specific material in an item of baggage comprising means to expose an area of the item to x-rays of at least two substantially different energy bands and detection means responsive to the x-rays passing through the item to generate for subareas over the exposed area respective sets of values representing the attenuation of the x-rays at each of the energy bands. Comparison means are employed which are operative on differences in attenuation between subareas in a neighborhood to determine the presence of a specific material in the neighborhood of the subareas and indicating means responsive to the comparisons for indicating presence of the specific material in the article. The comparison means comprise means for computing for a selected test subarea of the exposed area the values $(H_T, L_T)$ wherein $H_T$ is the logarithm of the attenuation of the x-rays at the higher energy band at the test subarea and $L_T$ is the logarithm of the attenuation of the x-rays at the lower energy band at the test subarea, and means for computing for a subarea nearby the test subarea the values $(H_B, L_B)$ wherein $H_B$ is the logarithm of the attenuation of the x-rays at the higher energy band at the nearby subarea and $L_B$ is the logarithm of the attenuation of the x-rays at the lower energy band at the nearby subarea. The comparison means are constructed to employ the values $(H_T, L_T)$ and $(H_B, L_B)$ in determining the presence of the specific material.

Preferably such a baggage inspection device features comparison means further comprising means for providing p-values P representing attenuation characteristics of various overlying materials, and means for associating a p-value $P_T$ with the values $(H_T, L_T)$ with the p-value $P_T$ proportional to the thickness of overlying materials at the test subarea, and means for associating a p-value $P_B$ with the values $(H_B, L_B)$ with the p-value $P_B$ proportional to the thickness of overlying materials at the nearby subarea. Such a device includes means for computing the value of $|(H_T-H_B)/(P_T-P_B)|=\Delta H/\Delta P$, and means for associating $\Delta H/\Delta P$ with a relative probability measure for the presence of the specific material at respective subareas.

In various preferred embodiments, the device includes means for examining the subareas and means responsive thereto for producing values for each subarea indicative of the relative probability of matching the specific material. The device includes means for displaying subareas over the exposed area of the ensemble, and means for highlighting those subareas having a probability greater than or equal to a selected threshold value of matching the specific material.

In other embodiments means are provided for computing the value of $(H_T-H_B)/(L_T-L_B)=K_{TB}$ and means are provided for comparing the value of $K_{TB}$ with the value of $K_{MAT}$ wherein $K_{MAT}$ is an attenuation characteristic of the specific material.

In preferred embodiments of the devices described so far where the x-ray source is polychromatic, $K_{MAT}=\mu_H(H_T,H_B,L_T,L_B)/\mu_L(H_T,H_B,L_T,L_B)$ wherein $\mu_H$, an attenuation coefficient of the specific material exposed to the higher energy x-rays, is a function of the logarithms of the attenuation of the x-rays at the test subarea and at the nearby subarea, and wherein $\mu_L$, an attenuation coefficient of the specific material exposed to the lower energy x-rays, is a function of the logarithms of the attenuation of the x-rays at the test subarea and at the nearby subarea. Preferably there are means for ascertaining whether the value of $K_{TB}$ is within a selected window of values of $K_{MAT}$, means for incrementing a respective counter if the value of $K_{TB}$ is within the window, means for examining the subarea counters and producing values for each subarea indicative of the relative probability of matching the specific material, means for displaying subareas over the exposed area, and means for highlighting those subareas having a probability greater than or equal to a selected threshold value of matching the specific material.

In preferred embodiments, the device possesses means to expose the area of the object further comprising an x-ray source, means for generating from the source x-rays of at least two substantially different energy bands, means for collimating a fan beam of the x-rays, and means for conveying the object to intercept the fan beam of the x-rays.

In various embodiments, the device is constructed specifically to detect a threat substance, an explosive, an illicit drug substance, a mineral of value, or a particular plastic. In some embodiments, the device is constructed to examine a stream of matter, which may for instance be comprised of rocks and the device is constructed to detect a mineral of value, or the stream can be shredded plastic refuse, and the specific material can be a particular form of plastic, such as halogenated hydrocarbon plastic to be separated from other plastic refuse. In other instances, the objects can be foodstuffs such as meat and the specific material can be bone or an inorganic contaminant.

Preferred embodiments of the devices described so far include means for locating edges in the exposed area where one material overlaps another, means for choosing subareas in close proximity to the edges to be the selected subareas, and means for assigning to the selected subareas a relative probability for the presence of the specific materials at the subareas based upon the comparisons with other subareas in the vicinity and/or neighborhood, the indicating means being responsive to the relative probability assignment.

Preferred embodiments of the inventions so far described further include means for dilating indications of subareas over regions whose edges have been determined to indicate the presence of the specific material. Such dilation makes the suspicious regions more prominently noticeable to an operator of the device, and the dilation enhances indication of presence of the specific material.

Our invention features, as well, a specific method of baggage inspection for detecting and indicating the probable presence of a specific material in an item of baggage and a device for implementing the method. The method comprises the steps of exposing the item to x-rays of at least two substantially different energy levels, generating for each subarea over the exposed area a set of data values representing logarithms of x-ray attenuation at the subarea at each of the energy levels, choosing a test subarea, filtering the data for the test subarea, averaging the data for the test subarea, processing the data for the test subarea to compute the values of $(H_T, L_T)$ for the test subarea, wherein $H_T$ is the logarithm of the attenuation of the x-rays at the test subarea at the higher energy level and $L_T$ is the logarithm of the attenuation of the x-rays at the test subarea at the lower energy level, and choosing a background subarea, filtering the data for the background subarea, averaging the data for the background subarea, processing the data for the background subarea to compute the values of $(H_B, L_B)$ for the background subarea, wherein $H_B$ is the logarithm of the attenuation of the x-rays at the background subarea at the higher energy level and $L_B$ is the logarithm of the value representing the attenuation of the x-rays at the background subarea at the lower energy level, and computing the value of $K_{TB}=(H_T-H_B)/(L_T-L_B)$, and comparing the value of $K_{TB}$ to the value of $K_{MAT}$, wherein $K_{MAT}=\mu_H(H_T,H_T,L_B,L_B)/\mu_L(H_T,H_B,L_T,L_B)$ wherein $\mu_H$, an attenuation coefficient of a specific material exposed to the higher energy x-rays, is a function of the logarithms of the attenuation of the x-rays at the test subarea and at the background subarea, wherein $\mu_L$, an attenuation coefficient of the specific material exposed to the lower energy x-rays, is a function of the logarithms of the attenuation of the x-rays at the test subarea and at the background subarea, and ascertaining whether the value of $K_{TB}$ is within a selected window of values of $K_{MAX}$, incrementing a respective counter if the value of $K_{TB}$ is within the window, choosing another background subarea, and iterating the steps from filtering the data for the background subarea to choosing another background subarea until a substantial number of background subareas have been so examined, and choosing another test subarea, and iterating the steps from filtering the data for the test subarea to choosing another test subarea until substantially all subareas have been so tested, and examining the subarea counters, producing values for each subarea indicative of the relative probability of matching the specific material, and displaying subareas over the area, and highlighting those subareas having a probability greater than or equal to a selected threshold value of matching the specific material.

Our invention features, in another aspect, a specific method of baggage inspection for detecting and indicating the probable presence of a specific material in an item of baggage and a device for implementing the method. The method comprises the steps of exposing the item to x-rays of at least two substantially different energy levels, generating for each subarea over the exposed area a set of data values representing logarithms of x-ray attenuation at the subarea at each of the energy levels, choosing a test subarea, filtering the data for the test subarea, averaging the data for the test subarea, processing the data for the test subarea to compute the values of $(H_T, L_T)$ for the test subarea, wherein $H_T$ is the logarithm of the attenuation of the x-rays at the test subarea at the higher energy level and $L_T$ is the logarithm of the attenuation of the x-rays at the test subarea at the lower energy level, and choosing a background subarea, filtering the data for the background subarea, averaging the data for the background subarea, processing the data for the background subarea to compute the values of $(H_B, L_B)$ for the background subarea, wherein $H_B$ is the logarithm of the attenuation of the x-rays at the background subarea at the higher energy level and $L_B$ is the logarithm of the value representing the attenuation of the x-rays at the background subarea at the lower energy level, providing p-values P representing attenuation characteristics of various overlying materials, associating a p-value $P_T$ with said values $(H_T, L_T)$ wherein said p-value $P_T$ is proportional to the thickness of overlying materials at said test subarea, associating a p-value $P_B$ with said values $(H_B, L_B)$ wherein said p-value $P_B$ is proportional to the thickness of overlying materials at said nearby subarea, computing the value of $|(H_T-H_B)/(P_T-P_B)|= 66 \, H/\Delta P$, associating $\Delta H / \Delta P$ with a relative probability measure for the presence of said specific material at respective subareas, storing said probability measure, choosing another background subarea, and iterating the steps from filtering the data for the background subarea to choosing another background subarea until a substantial number of background subareas have been so examined, and choosing another test subarea, and iterating the steps from filtering the data for the test subarea to choosing another test subarea until substantially all subareas have been so tested, and examining the subarea probability measure stores, producing values for each subarea indicative of the relative probability of matching the specific material, and displaying subareas over the area, and highlighting those subareas having a probability greater than or equal to a selected threshold value of matching the specific material.

Preferably the methods described so far further include employing computed tomographic information to detect the specific material that may be present in subareas indicated by the computer-processed dual energy information as being probable subareas for the presence of the specific materials.

Our invention features, in general, a system for accurately discriminating specific substances in an x-ray image of an object (such as an article of baggage), despite the presence of overlying unknown background substances. In general, our invention features the discrimination of arbitrary (which may be low-Z) materials in the presence of an unknown background composed of a mix of overlying low-Z or high-Z materials.

With this invention, the ability is gained to discriminate different types of plastics or plastic-like materials such as plastic explosives (C4, RDX, etc.) and other kinds of explosives (TNT, DYNAMITE, etc.) from innocuous materials in baggage, cargo, letters and small parcels, or other objects to be inspected despite, and in the presence of, overlying objects and materials.

In another aspect our invention features the discrimination of low-Z materials such as drugs (i.e. cocaine, heroin, marijuana, . . . ).

In another aspect our invention features the discrimination of specific plastic material from other plastic materials of different composition.

In another aspect our invention features the discrimination of foreign materials in foods or foodstuffs or other manufactured items.

In preferred embodiments the object to be examined is transported past the x-ray beam on a conveyor or other slider mechanism as the x-ray beam at two energy bands scans the object item and the attenuated x-rays are converted by a detector array into a series of x-ray attenuation values which are then processed with a computer system to discriminate one or more specific substances in the object. If a sufficient amount of a specific material is detected, an alarm is triggered and a visual display device displays the pixels containing the suspect specific materials in a color (e.g., RED) over a normal black-and-white x-ray image. Additional image enhancement algorithms can be applied to the displayed image under control of an operator's console that can include zoom, contrast enhancement, color processing algorithms, such as the low-Z/high-Z ratio image, and other enhancements to provide additional information to the operator to aid in threat discrimination where threats may be defined as weapons as well as explosive substances and mechanisms.

In the following disclosure of preferred embodiments, the attenuation values of the x-rays are described as being measured at 'pixels' but more generally, the attenuation values can be measured at 'subareas' of the area exposed to x-rays, not necessarily at given picture elements (pixels). Similarly, the specific material to be detected is often a threat substance such as bomb material, but the present invention is not limited to apply only to bombs.

Other advantages and features of the invention will be apparent from the following description of preferred embodiments and from the claims.

DESCRIPTION OF PREFERRED EMBODIMENTS

The drawings are first briefly described.

Figures 9A, 9B, 9C:
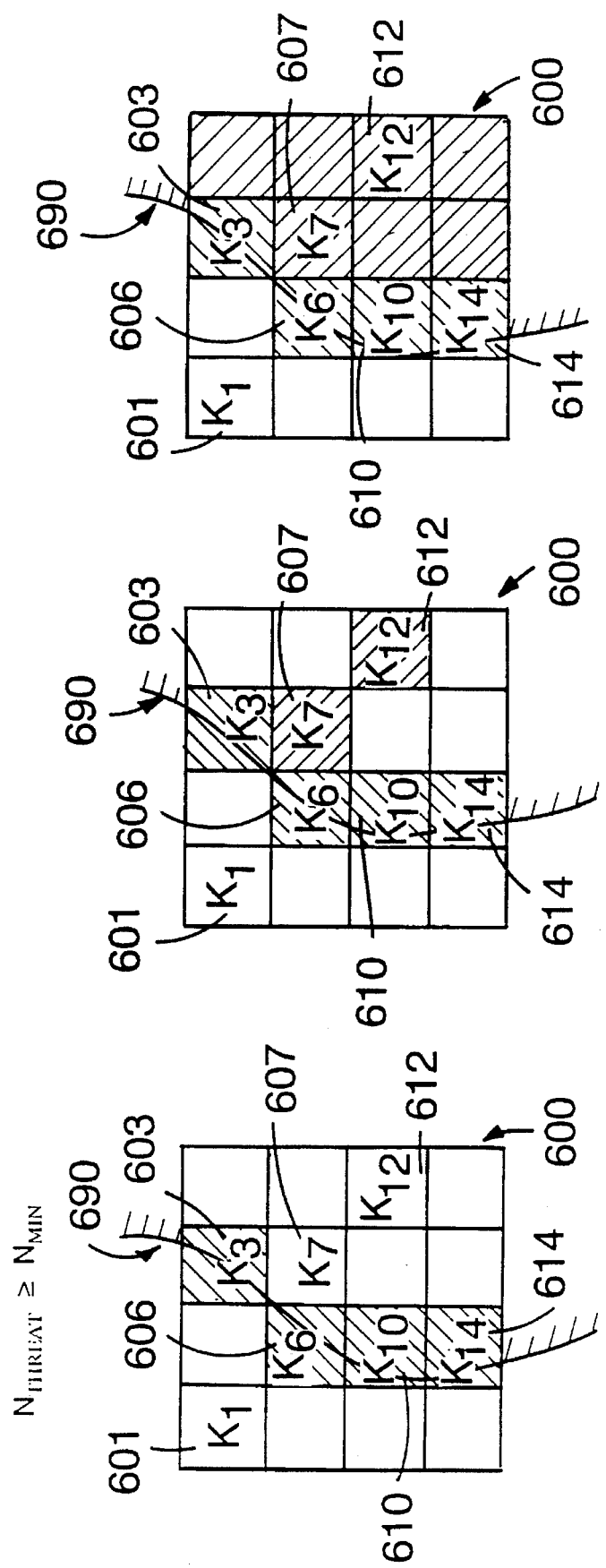

FIGS. 9(a)–(c) depict luminance dilation algorithm effects.

Figure 10:
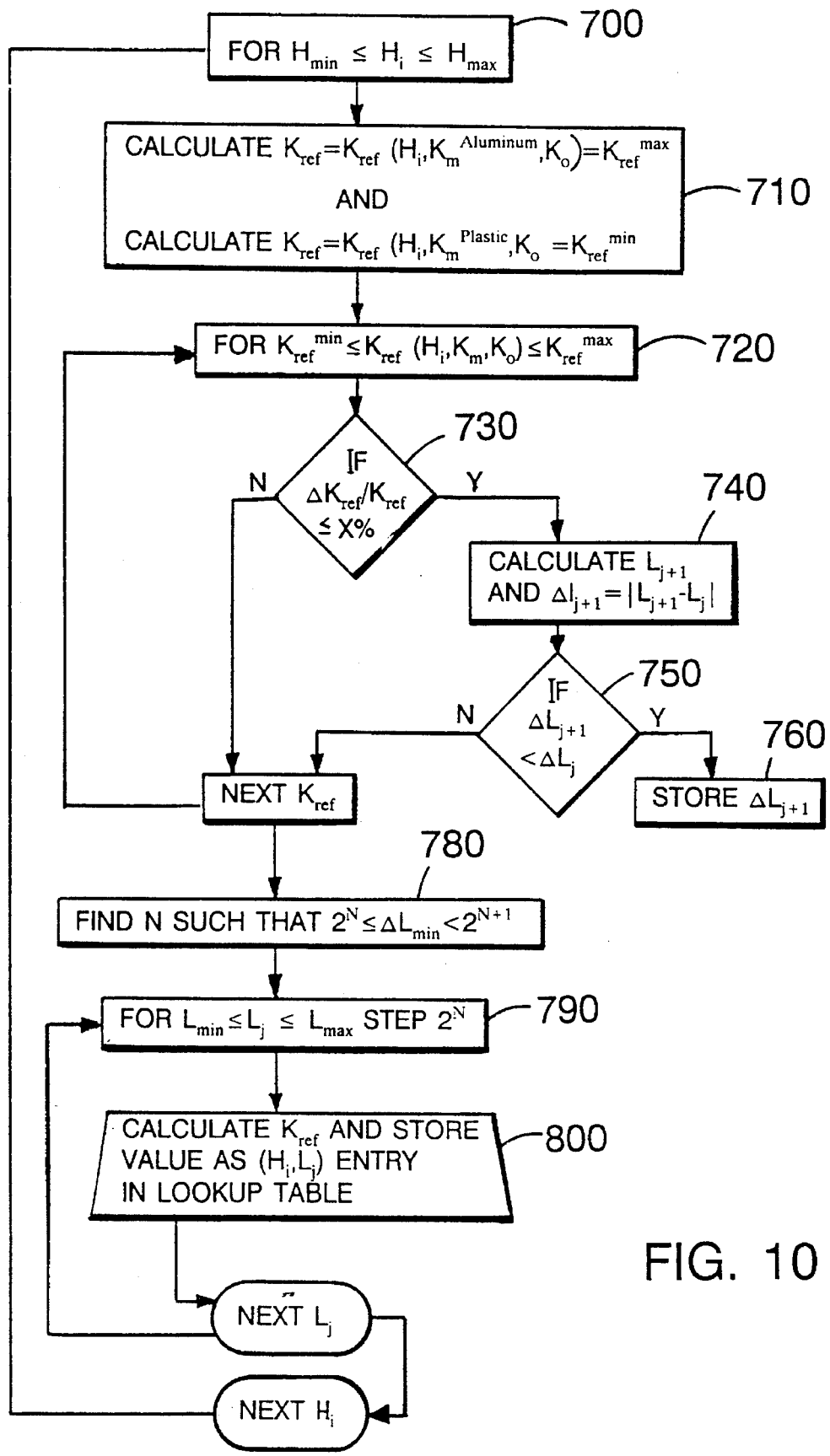

FIG. 10 is a flow diagram for generating a lookup table.

Figure 11:
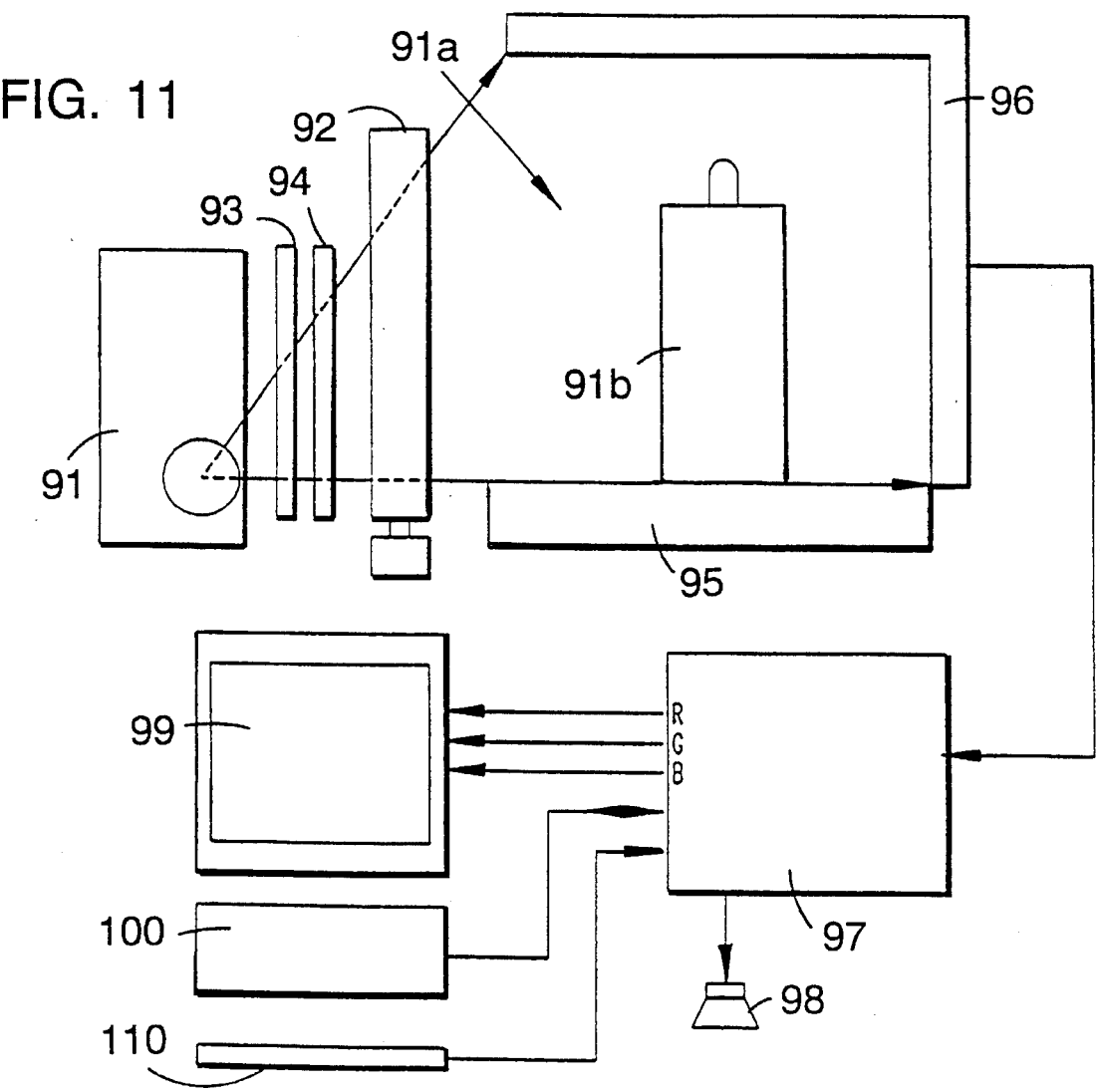

FIG. 11 illustrates diagrammatically a preferred device in its entirety.

Figure 12:
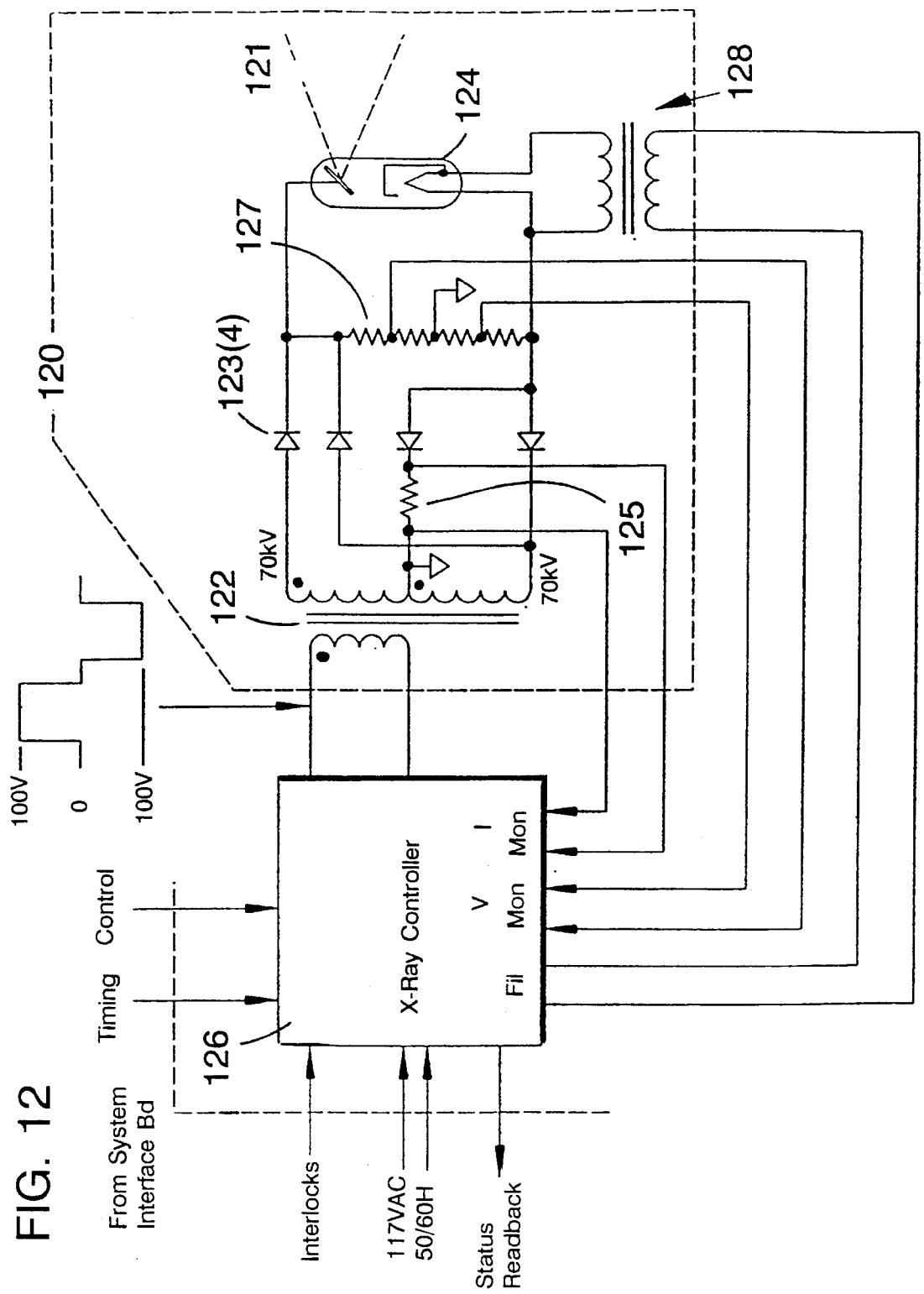

FIG. 12 is a circuit diagram of the x-ray source assembly of FIG. 11.

FIGS. 13a–13d illustrate the calibration shuttle assemblies.

FIGS. 14a–14c illustrate the x-ray filter drum and timing wheel details.

Figure 15:
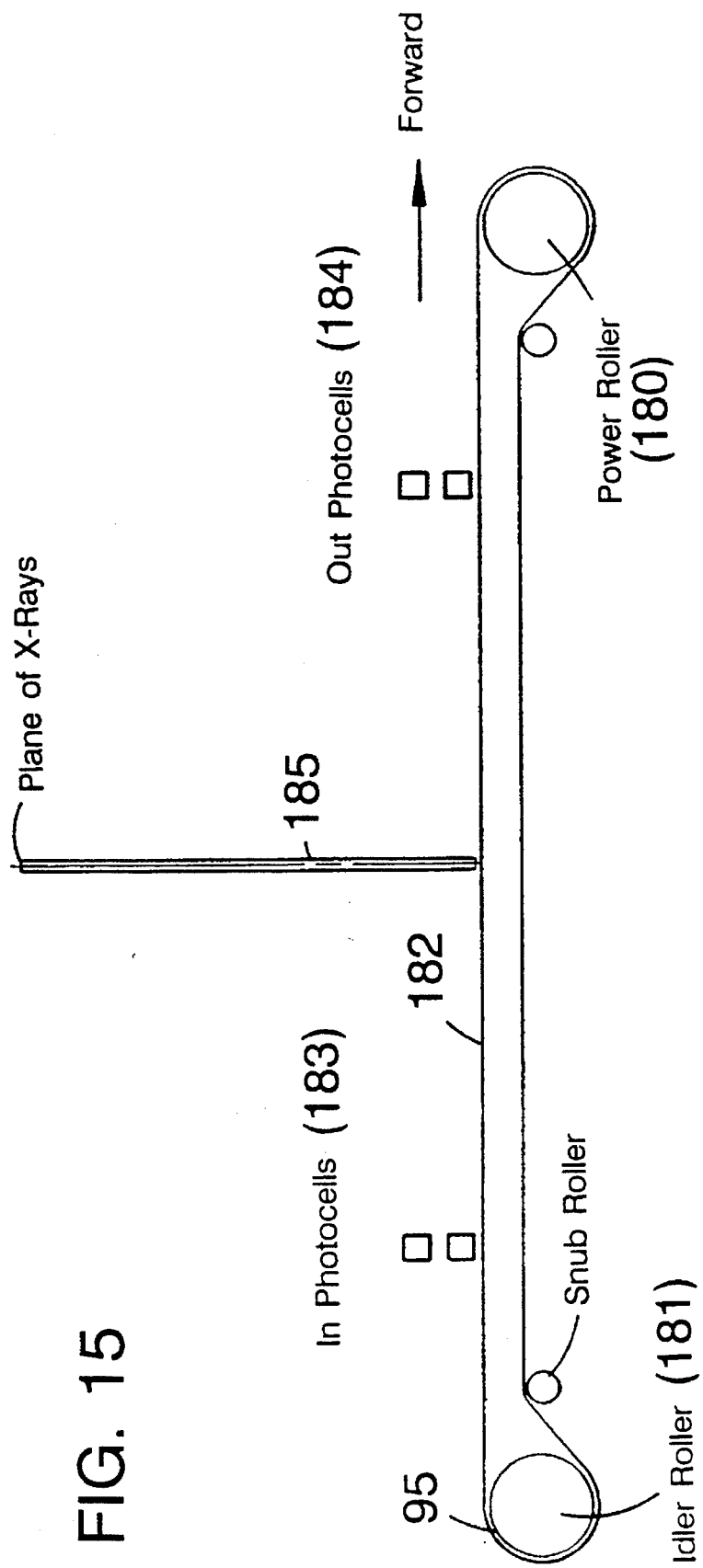

FIG. 15 illustrates the conveyor, belt, and baggage detection photocell assembly of FIG. 11.

Figure 16A:
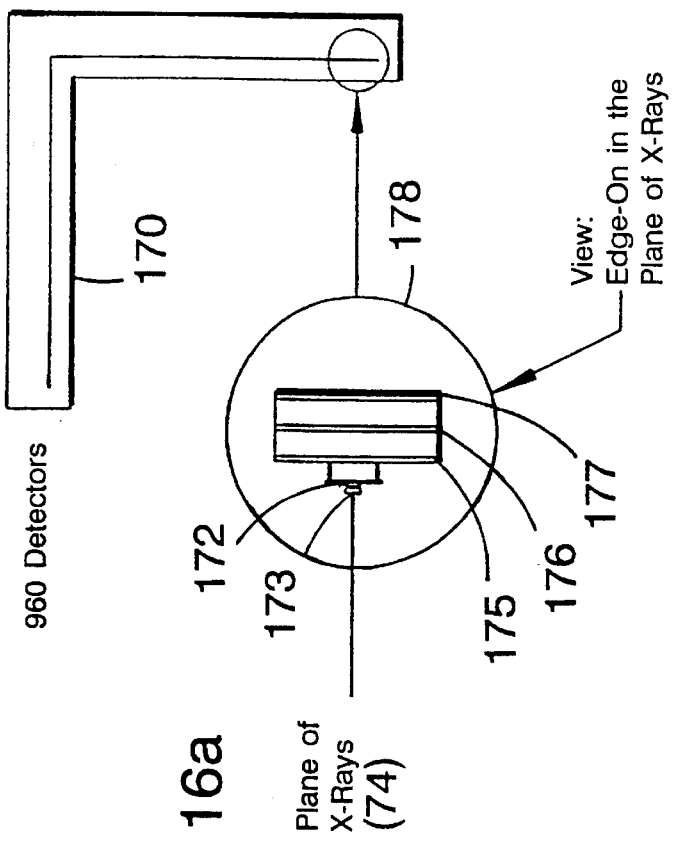
Figure 16B:
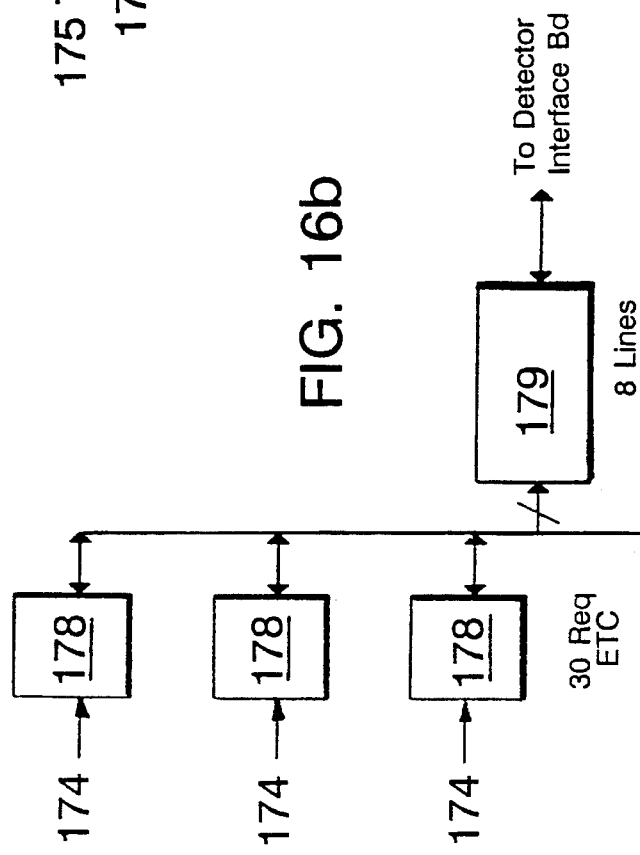

FIGS. 16a and 16b illustrate the design and construction of the x-ray detector array of FIG. 11.

Figure 17:
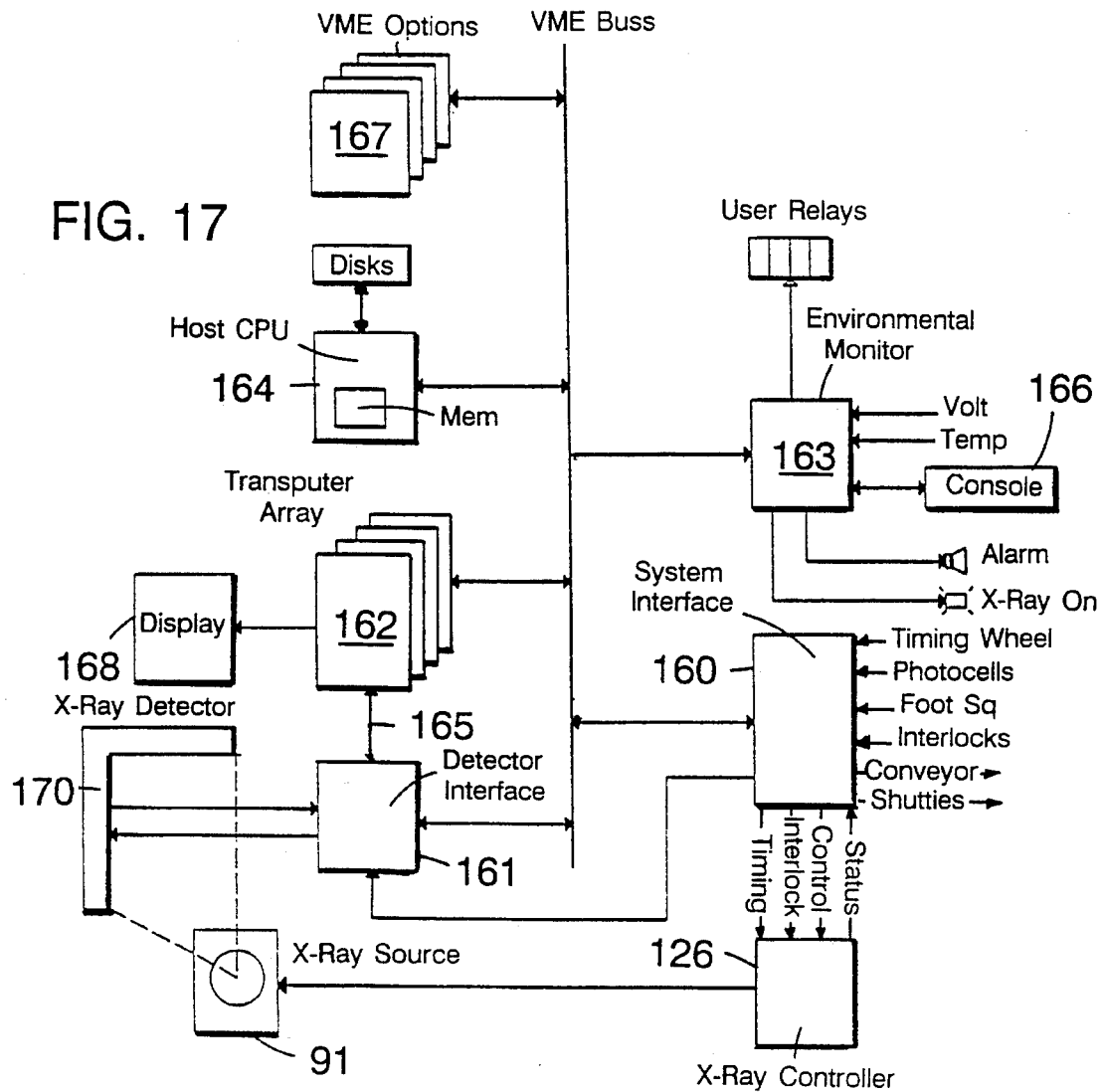

FIG. 17 details the major functional blocks comprising the x-ray system of FIG. 11.

Figure 18A:
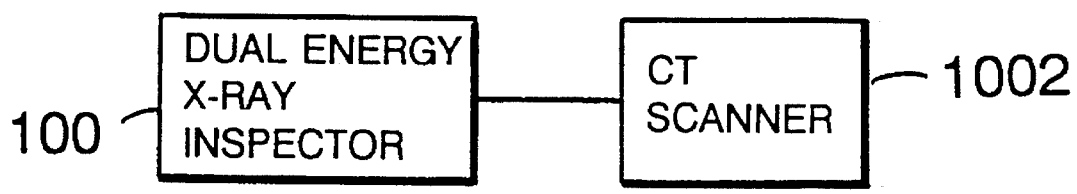
Figure 18B:
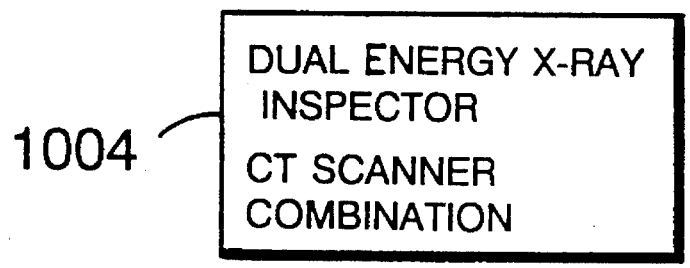

FIGS. 18a and 18b illustrate preferred embodiments employing computed tomography with a dual energy x-ray inspector.

Figure 19:
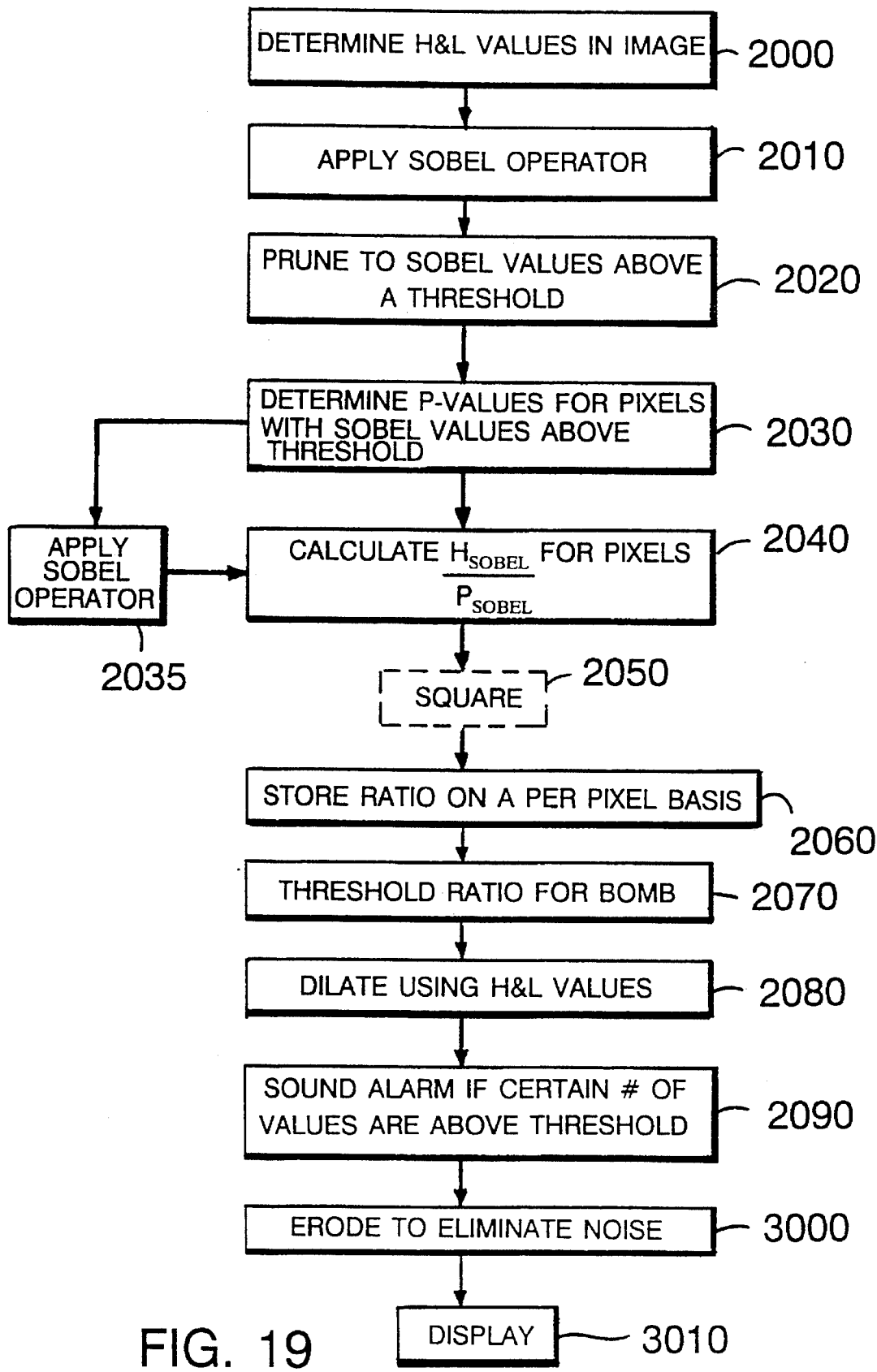

FIG. 19 is a flow diagram for a preferred detection algorithm.

Figure 20:
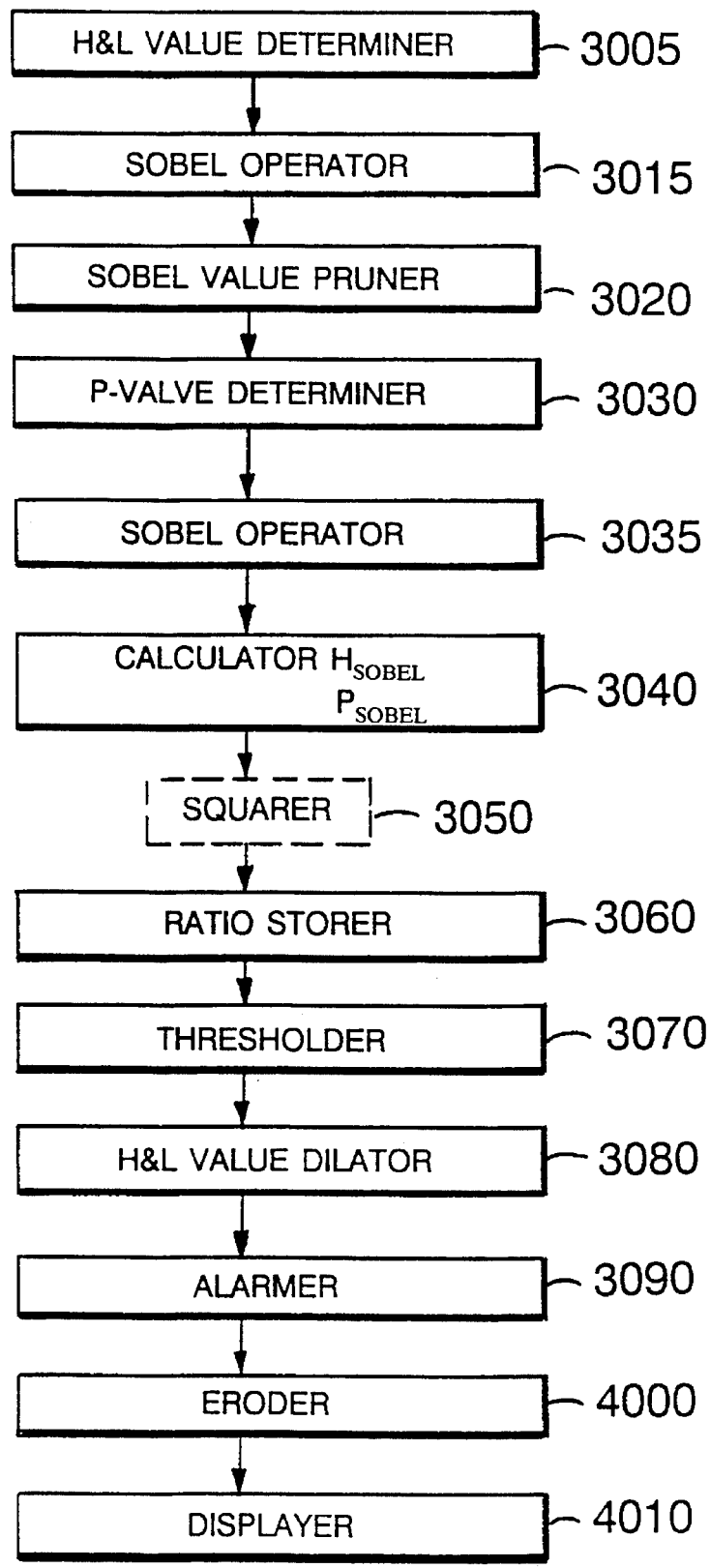

FIG. 20 is a schematic diagram for a device that dan implement the preferred detection algorithm given in FIG. 19.

EMBODIMENT EMPLOYING MONOENERGETIC X-RAYS

Figure 1:
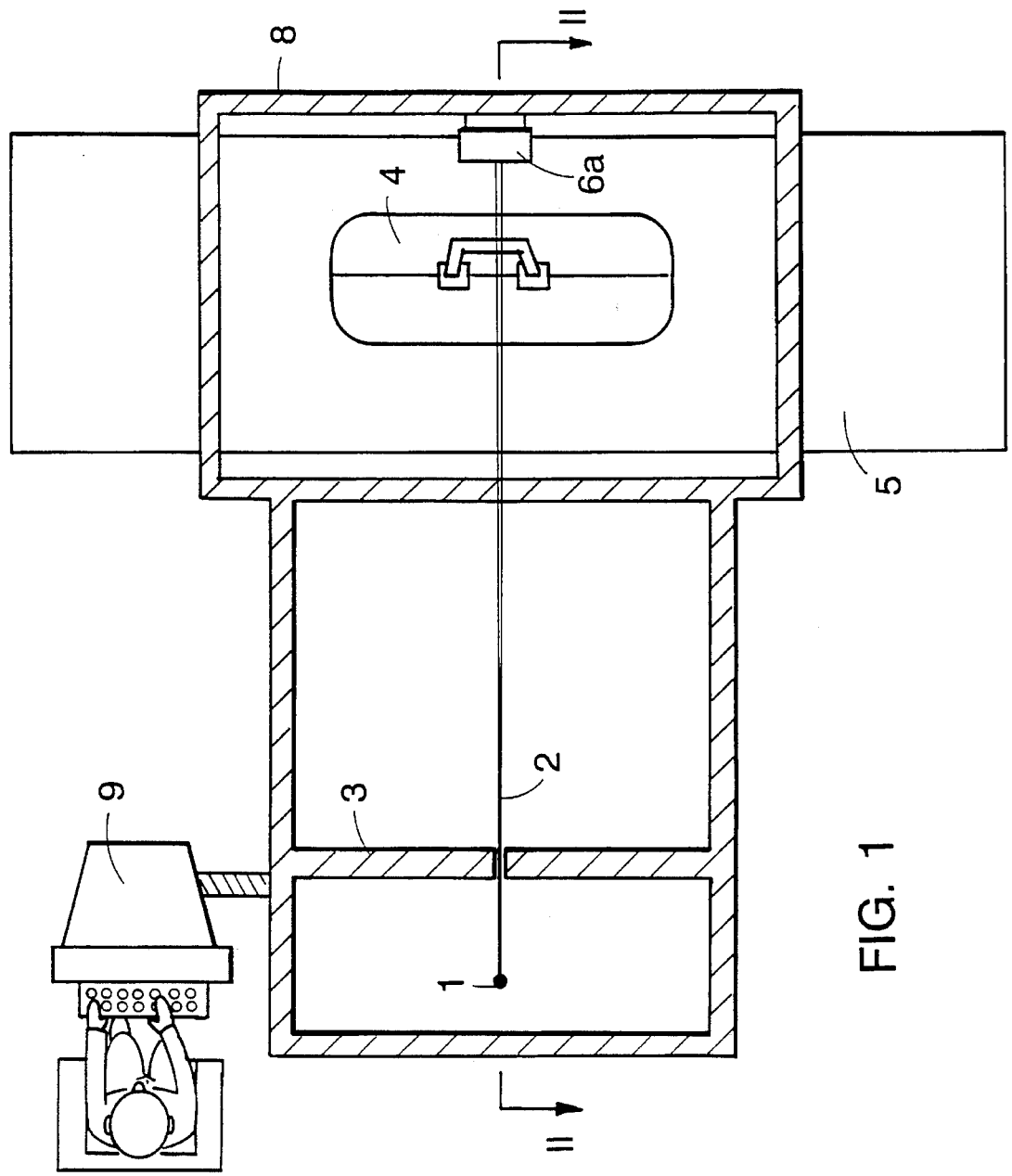
FIG. 1 is a schematic plan view of a device capable of baggage inspection.
Figure 2:
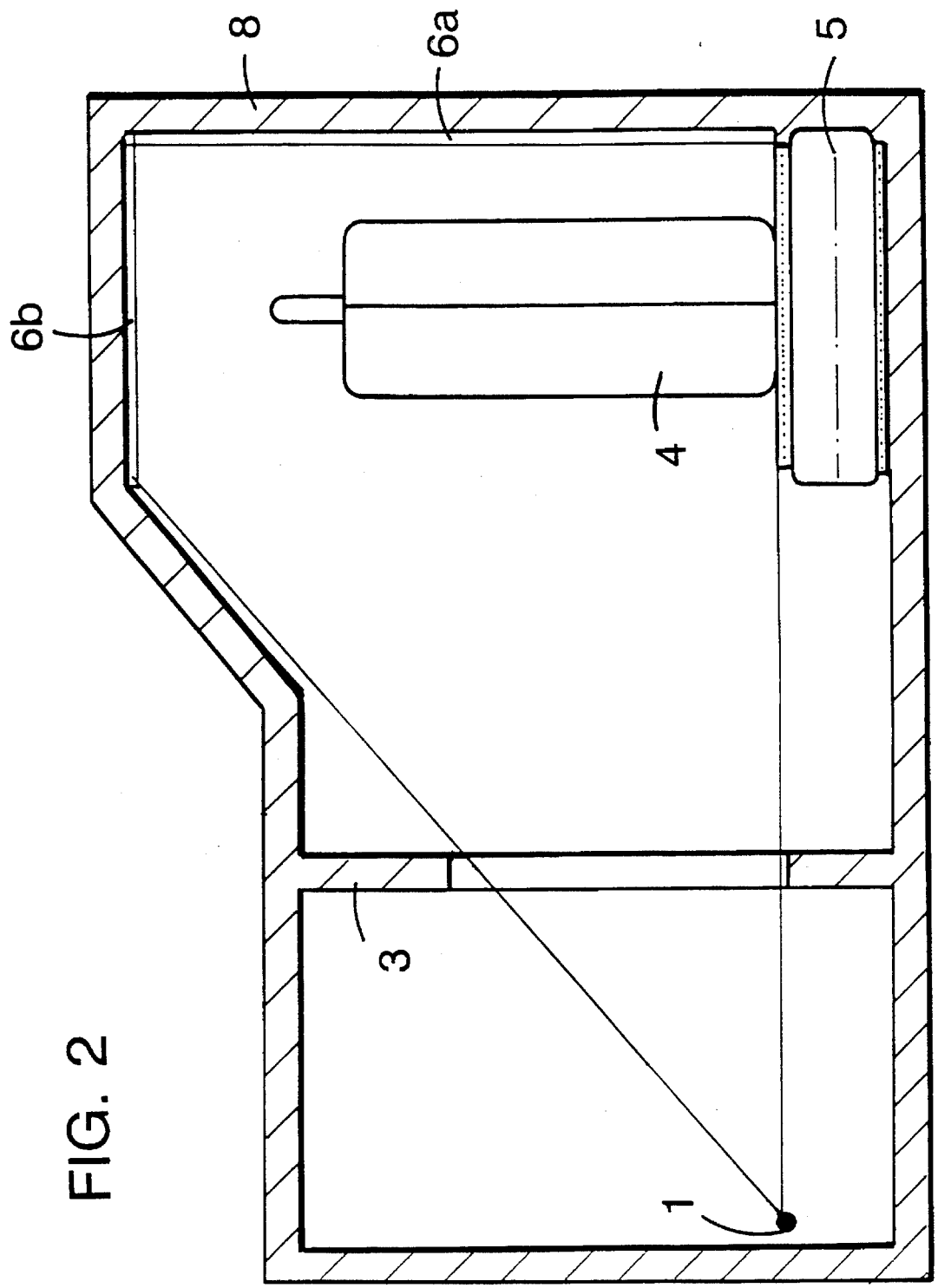
FIG. 2 is a side view cross section along line II—II in FIG. 1.
Figure 3:
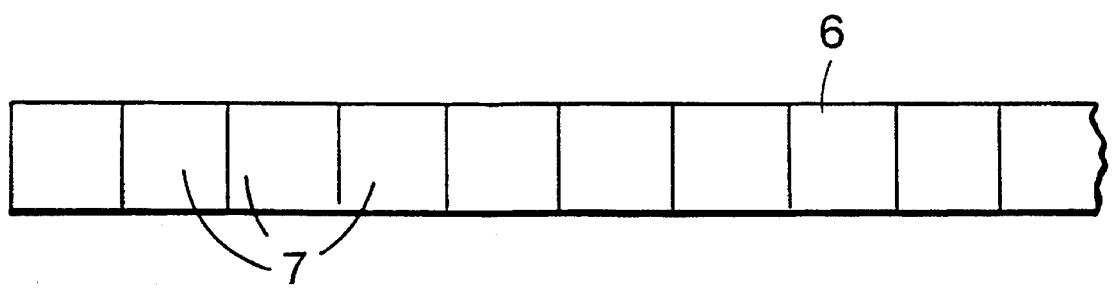
FIG. 3 shows a strip detector used in the device of FIG. 1.

As shown in FIGS. 1 and 2, an x-ray source 1 produces a beam of x-rays at two substantially different energies, two energy bands so narrow that each is effectively monoenergetic. The source is spaced from the front of a shielding tunnel 8 in position to expose objects within the tunnel. The beam is collimated in the fan beam collimator 3 made of lead or another material of sufficient thickness to stop x-rays. The resulting fan beam 2 encounters articles 4 such as pieces of luggage and baggage moved through the beam path by a conveyor 5, within shielding tunnel 8. The attenuated beam of x-rays reaches a strip detector array 6, shown in more detail in FIG. 3, made up of a series of individual x-ray detectors 7 of approximate dimensions 2 mm×3 mm each made of a scintillation crystal coupled to a photodiode. The detector array 6 comprises two parts 6a and 6b (FIG. 2) forming two sides of the tunnel 8, in the embodiment shown, at the back and top of the tunnel.

The x-ray source 1 alternates between high energy and low energy in order to obtain, for each pixel, measurements of x-ray attenuation at both energies. Because of continuing movement of the conveyor, the precise points of exposure of the object for a given ray at the alternate high and low energy will be slightly offset, but the points can be treated as being the same pixel because of their proximity. (In another embodiment, as where reduced accruacy can be tolerated, the x-ray source may simultaneously produce x-rays of both the high and low energy and two sets of superposed detectors can be used, one set sensitive to high energy x-rays, the other set sensitive to low energy x-rays, giving simultaneous detection of x-ray attenuation at both energies at the same point.)

An attenuation measurement is taken for each pixel simply as the ratio $I/I_o$ of detected x-ray intensity I at the detector 6 (attenuated by the object) to the unattenuated x-ray intensity $I_o$ measured at detector 6 in the absence of the object, e.g. between articles on the conveyor 5. A convenient quantity characterizing the attenuation is the negative natural logarithm of the ratio $I/I_o$. Consequently, we define:

$$H=-\ln(I^H/I_o^H)=\ln(I_o^H/I^H)=\ln(I_o^H)-\ln(I^H), \quad (1)$$

where $I^H$ and $I_o^H$ are respectively the high energy x-ray intensity at the detector 6 and the high energy incident x-ray intensity. Similarly, we define:

$$L=-\ln(I^L/I_o^L)=\ln(I_o^L/I^L)=\ln(I_o^L)-\ln(I^L), \quad (2)$$

where $I^L$ and $I_o^L$ are, respectively, the low energy x-ray intensity at the detector 6 and the low energy incident x-ray intensity.

The present embodiment acquires such attenuation data over the region exposed to the fan beam and processes it by a comparison technique to find whether or not a specific material (an explosive, e.g.) is present in the article 4 of baggage without knowing beforehand whether the specific material is present or where the material is located, and without knowing the composition of the other materials in the article 4.

To do this, the embodiment is constructed to acquire, for substantially all pixels over the exposed region of the article 4, pairs of attenuation valves (H,L) and compare the values between pairs of nearby pixels to test whether differences in attenuation at the different pixels can be attributed to the presence of a specific material.

The algorithmic efficiency is substantially enhanced by applying an edge finding algorithm, such as the Sobel edge finding algorithm that can be found in standard image processing references, to the pixel data. The binary pixel comparisons are then performed primarily on the set of pixels within a given distance of an edge found in the image data. Subjecting the detected x-ray data to an edge finding or gradient evaluating algorithm is generally useful in substantially all embodiments described herein.

Figure 4:
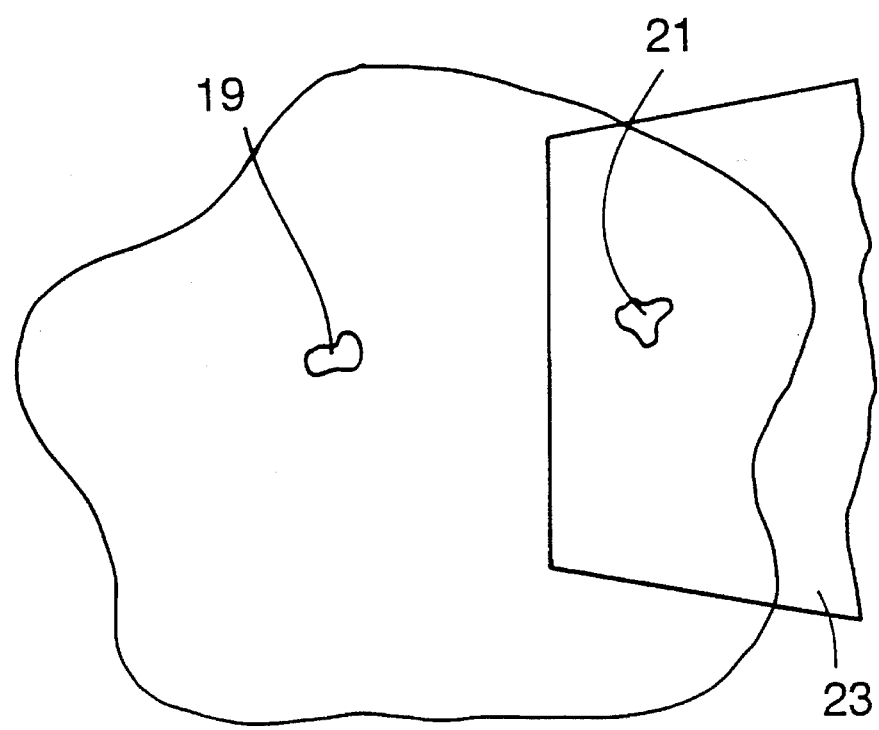
FIG. 4 illustrates various areas and subareas in the x-ray image of an exposed object.

Consider, as in FIG. 4, a typical pixel 19, assumed to be a background pixel. Identify with pixel 19 the attenuation values $(H_B, L_B)$. Consider a nearby pixel 21 as a test pixel and identify with pixel 21 the attenuation values $(H_T, L_T)$. Calculate the quantity $$(H_T-H_B)/(L_T-L_B)=K_{TB}. \quad (3)$$

Let $\mu_H$ be the attenuation coefficient of high energy x-rays for the specific material of interest and let $\mu_L$ be the attenuation coefficient of low energy x-rays for the specific material of interest. Compare the value of $K_{TB}$ calculated for pixels 19 and 21 to the value of $\mu_H/\mu_L$. If $K_{TB}$ equals $\mu_H/\mu_L$, then the difference in attenuation between pixels 19 and 21 can be attributed to the presence of the specific material of interest at pixel 21 and a record of the successful match is made for pixel 21. If $K_{TB}$ is not equal to $\mu_H/\mu_L$, then no attribution is made. The inter-pixel spacing is generally small enough (resolution high enough) that there is a likelihood that the only substantial difference between the materials encountered by the x-rays passing through pixels 19 and 21 is a certain thickness of the specific material of interest present at pixel 21 and absent at pixel 19, the other background materials being essentially the same for both pixels. In FIG. 4, a layer of explosive material 23 is shown to overlie pixel 21 and $K_{TB}=\mu_H/\mu_L$.

This comparison process is repeated for all other background pixels in the neighborhood of test pixel 21 and then a different test pixel is substituted for test pixel 21, and compared with another set of background pixels in its neighborhood, until substantially all pixels in the exposed region of the article 4 have been treated as test pixels. The pixel records of successful matches with the specific material of interest are reviewed, over the area examined, by an automatic system that applies statistical criteria to judge whether the specific material of interest is likely to be present and if so, the relevant pixels in the image, displayed on a monitor 9 as shown in FIG. 1, are highlighted or indicated in red or a bright, distinguishing color. Comparisons for a number of specific materials and their presence can be highlighted or indicated in the same or a distinctive manner.

Figure 5:
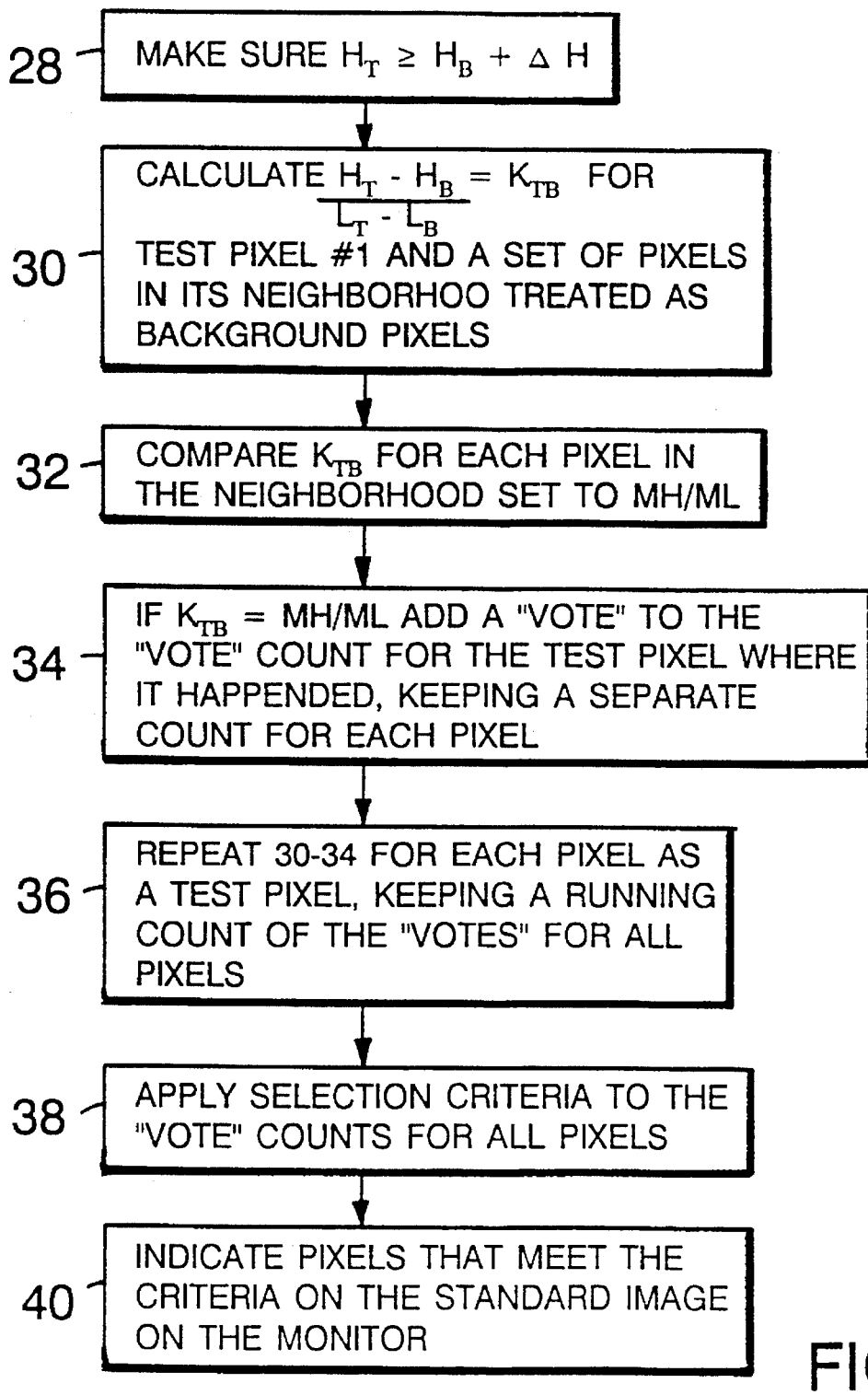
FIG. 5 is a flow diagram for a monoenergetic detection algorithm.

The detection algorithm for the present monoenergetic embodiment is given schematically in FIG. 5. The first step (30) is to calculate $K_{TB}=(H_T-H_B)/(L_T-L_B)$ for test pixel #1 and a set of nearby pixels in the neighborhood of test pixel #1 treated as background pixels. Then (32), the value $K_{TB}$ when testing the test pixel #1 against each background pixel in the set is compared to $\mu_H/\mu_L$ for the specific material(s) of interest. If $K_{TB}=\mu_H/\mu_L$, a "vote" is added (34) to the "vote" count associated with the test pixel, keeping a separate count for each pixel. This whole procedure (30)–(34) is to be repeated (36) for each pixel as a test pixel, keeping a running count of "votes" for all test pixels. Then, selection criteria, such as whether or not the number of "votes" for a pixel exceed a threshold value, are applied (38) to the "vote" counts for all pixels. Finally (40), pixels that meet the selection criteria are indicated and distinguished in the standard image on the monitor.

In conducting the above algorithm, for computational efficiency, for any comparison in which the value $H_T$ is less than $H_B$ (or not greater than $H_B$ by an amount related to the accuracy of the system and the nature of the material being detected), the computation is not performed, and no vote is assigned (28).

Figure 6:
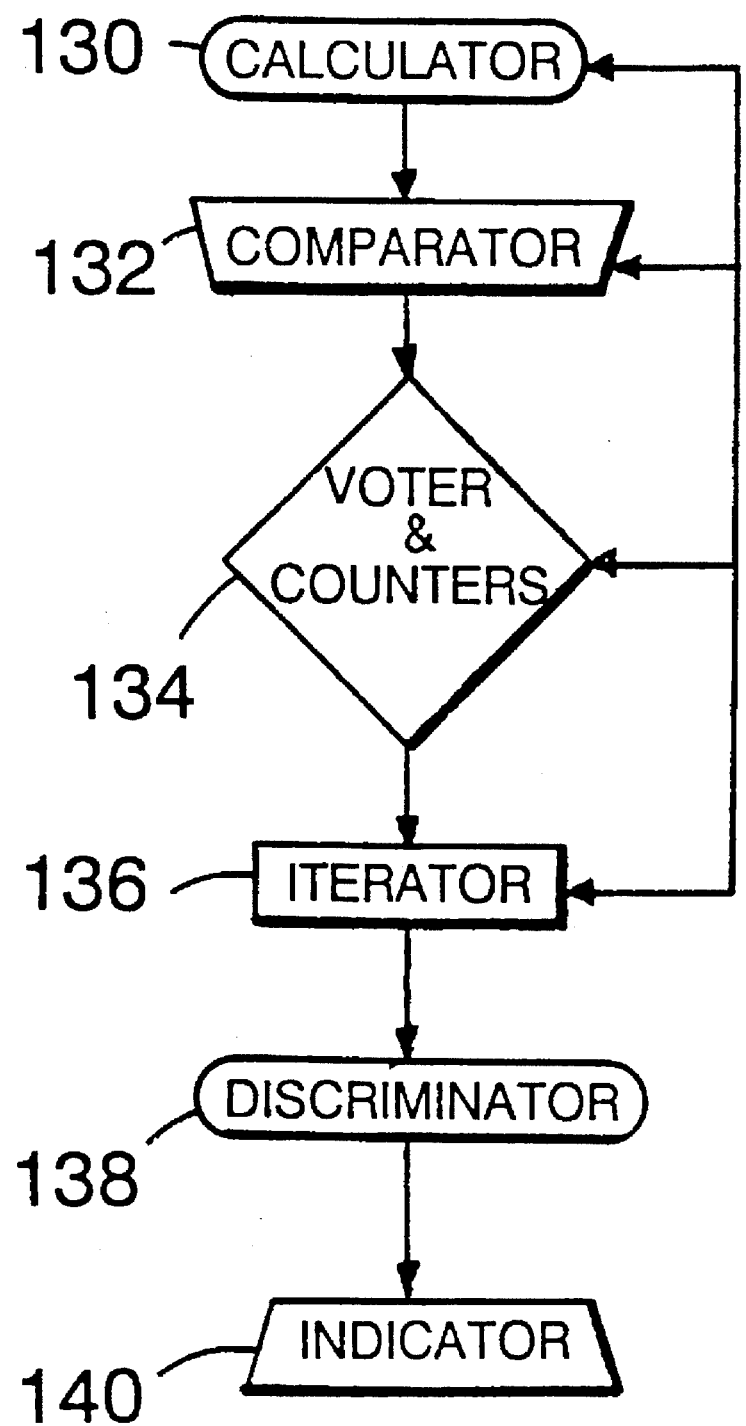
FIG. 6 is a schematic diagram for a device that can implement the monoenergetic and polychromatic detection algorithms.

A detector device embodying the detection algorithm of FIG. 5 is shown in FIG. 6. A calculator 130 calculates $K_{TB}=(H_T-H_B)/(L_T-L_B)$ for test pixel #1 and a set of nearby pixels in the neighborhood of test pixel #1 treated as background pixels. A comparator 132 takes the output of calculator 130 and compares the value $K_{TB}$ for each background pixel in the set nearby test pixel #1 to $\mu_H/\mu_L$ for the specific material(s) of interest. If $K_{TB}=\mu_H/\mu_L$, the comparator 132 alerts a voter 134 which then adds a "vote" to the "vote" count associated with the nearby pixel, keeping a separate count for each pixel. An iterator 136 activates the calculator 130, comparator 132, and voter 134 so that the detector device operates on each pixel as a test pixel, keeping a running count of "votes" for all pixels. The output of the iterator 136 is input to a discriminator 138 which applies selection criteria to the "vote" counts for all pixels. Pixels that meet the selection criteria are passed on to an indicator 140 where they are distinguished in the standard image on the monitor.

Polychromatic X-Ray Embodiment

The polychromatic x-ray case must be considered when the x-ray source delivers x-rays in energy bands that are too broad to be considered monoenergetic. Then the attenuation coefficients $\mu_H$ and $\mu_L$ are no longer approximately constant characteristics of specific materials, but generally become functions of the x-ray attenuation values measured at high and low energies. For example, $$\mu_H=\mu_H(H_T, L_T, H_B, L_B), \text{ and} \quad (4a)$$

$$\mu_L=\mu_L(H_T, L_T, H_B, L_B) \quad (4b)$$

where all attenuation values $(H_T,L_T,H_B,L_B)$ have been compensated for the intervening air when the article of baggage is absent. (Such air corrected attenuation values are zero when nothing is in the beam.) The ratio $K_{MAT}=\mu_H(H_T,L_T,H_B,L_B)/\mu_L(H_T,L_T,H_B,L_B)$ is then generally also a function of the attenuation values, $K_{MAT}=K_{MAT}(H_T,L_T,H_B,L_B)$. In the preferred embodiment, a lookup table for the function $K_{MAT}$ is generated empirically and an interpolation formula is used to furnish values for $K_{MAT}$ at any values of its arguments.

As in the embodiment employing monoenergetic x-rays, embodiments employing polychromatic x-rays are constructed to acquire, for substantially all pixels over the exposed region of the article 4 (FIGS. 1 and 2), pairs of attenuation values (H,L) and compare the values between pairs of nearby pixels to test whether differences in attenuation at the different pixels can be attributed to the presence of a specific material. Consider again, as in FIG. 4, a typical pixel 19, assumed to be a background pixel. Identify with pixel 19 the attenuation values $(H_B,L_B)$. Consider again a nearby pixel 21 as a test pixel and identify with pixel 21 the attenuation values $(H_T,L_T)$. Once more, calculate the quantity $$(H_T-H_B)/(L_T-L_B)=K_{TB}. \quad (5)$$

Now, however, the value of KTB calculated for pixels 19 and 21 is to be compared to the value of $K_{MAT}(H_T,L_T,H_B,L_B)=\mu_H(H_T,L_T,H_B,L_B)/\mu_L(H_T,L_T,H_B,L_B)$ which is found by consulting the lookup table and applying the interpolation formula. Again, if $K_{TB}=K_{MAT}(H_T,L_T,H_B,L_B)$, then the difference in attenuation between pixels 19 and 21 can be attributed to the presence of the specific material of interest at pixel 21 and a record of the successful match is made for pixel 21, whereas if $K_{TB}$ is not equal to $K_{MAT}$, then no attribution is made. In FIG. 4, a layer of explosive material 23 still overlies pixel 21 and $K_{TB}=K_{MAT}(H_T,L_T,H_B,L_B)$ for polychromatic embodiments.

In both the embodiment employing monoenergetic x-rays and in embodiments employing polychromatic x-rays, "equality" between two values is taken to mean that both values lie within a certain window of values. Two values that do not lie within a certain window of values of each other are "unequal". For example, if a specific bomb material of interest is the high explosive C4, manufactured to military specifications and hence fairly uniform, $K_{MAT}$ is about 0.6 and the window of values is narrow, plus or minus 0.01 from the central $K_{MAT}$ value 0.6. Narrower windows, such as plus or minus 0.001 from the central $K_{MAT}$ value 0.6 are possible, but the smaller the window, the fewer the "votes" and the ability to discriminate between real bomb material and innocuous material lessens which is not desirable. On the other extreme, if the specific material of interest is a water gel explosive, $K_{MAT}$ is again about 0.6 but the window of values is wider, plus or minus 0.03 from the central $K_{MAT}$ value 0.6. Similarly, Semtex is very C4-like but varies widely in its manufacture because of many different manufacturers using different kinds of oil, for example, and so Semtex like water gels, requires a wider window than C4. The appropriate size of window is determined on a per substance basis.

The process of comparison of $K_{TB}$ to $K_{MAT}(H_T,L_T,H_B,L_B)$ is repeated for all other background pixels in the neighborhood of test pixel 21. The neighborhood can be a square region 1.5 inches to a side optimized to allow for spatial variations in the contents of the piece of luggage being inspected. Then, a different test pixel is substituted for pixel 21, and compared with another set of background pixels in its neighborhood, until substantially all pixels in the exposed region of the article 4 have been treated as test pixels. As in the embodiment employing monoenergetic x-rays, the pixel records of successful matches with the specific material of interest are reviewed, over the area examined, by an automatic system that applies statistical criteria to judge whether the specific material of interest is likely to be present and if so, the relevant pixels in the image are highlighted or indicated in red or a bright, distinguishing color. Comparisons for a number of specific materials and their presence can be highlighted or indicated in the same or a distinctive manner.

Figure 7:
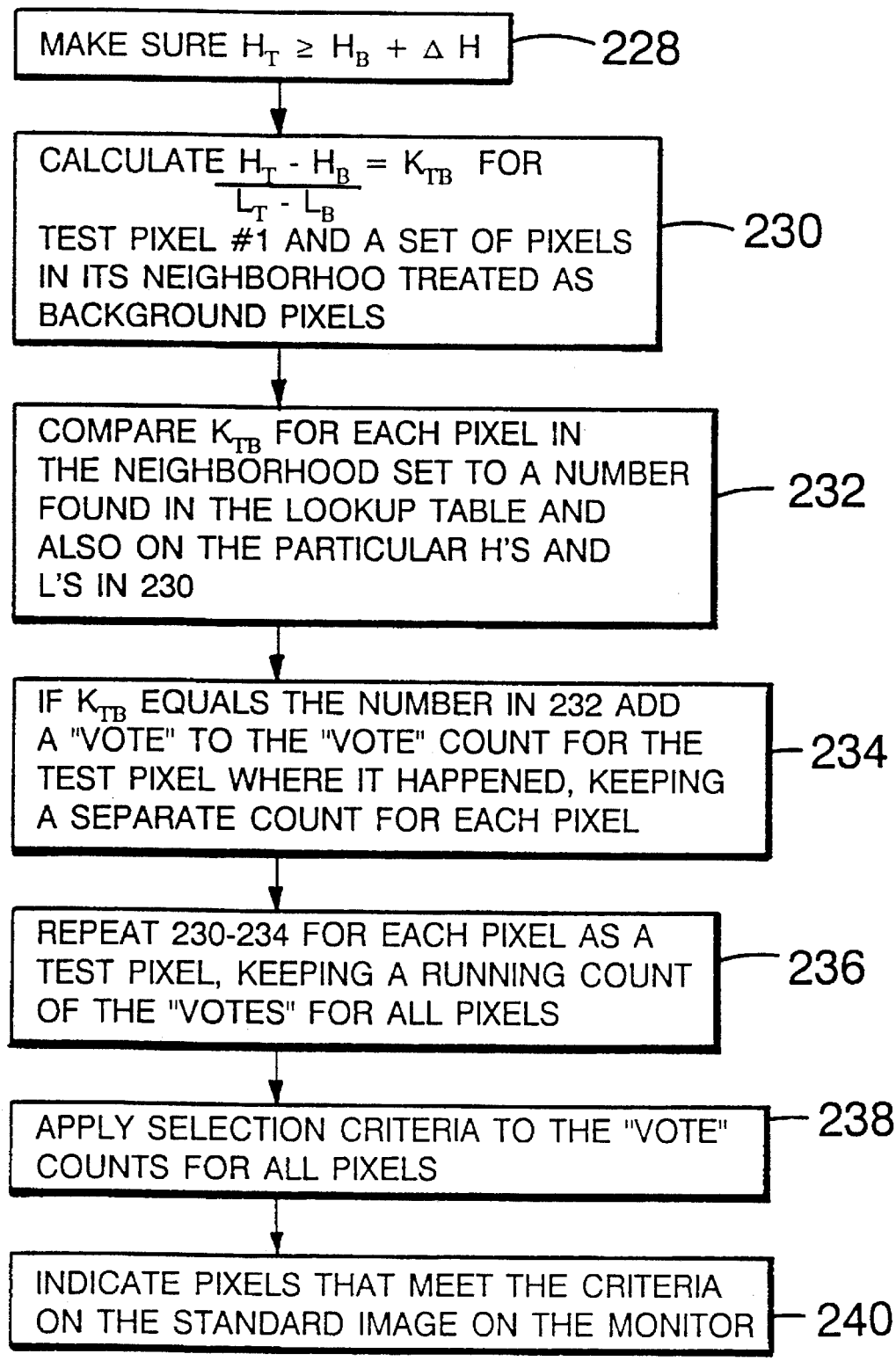
FIG. 7 is a flow diagram for a polychromatic detection algorithm.

The detection algorithm for a polychromatic embodiment is given schematically in FIG. 7. The first step (228) is to make sure that the computation is to be performed. The next step (230) is to calculate $K_{TB}=(H_T-H_B)/(L_T-L_B)$ for test pixel #1 and a set of nearby pixels in the neighborhood of test pixel #1 treated as background pixels. Then (232), the value $K_{TB}$ for each background pixel in the set nearby test pixel #1 is compared to a specific number found in the lookup table which depends on $\mu_H(H_T,L_T,H_B,L_B)/\mu_L(H_T,L_T,H_B,L_B)$ for the specific material(s) of interest, and also on the attenuation values (H,L) for test pixel #1 and nearby background pixels in the neighborhood of test pixel #1. If $K_{TB}$ equals this specific number, a "vote" is added (234) to the "vote" count associated with the nearby pixel, keeping a separate count for each pixel. This whole procedure (230)–(234) is to be repeated (236) for each pixel as a test pixel, keeping a running count of "votes" for all pixels. Then, selection criteria, such as whether or not the number of "votes" for a pixel exceed a threshold value, are applied (238) to the "vote" counts for all pixels. Finally (240), pixels that meet the selection criteria are indicated and distinguished in the standard image on the monitor.

The detector device shown in FIG. 6 is also used for polychromatic embodiments by modifying the comparator 132. In the polychromatic case, the comparator 132 takes the output of calculator 130 and compares the value of $K_{TB}$ for each background pixel in the set nearby test pixel #1 to a specific number found in the lookup table which depends on $\mu_H(H_T,L_T,H_B,L_B)/\mu_L(H_T,L_T,H_B,L_B)$ for the specific material(s) of interest, and also on the attenuation values (H,L) for test pixel #1 and nearby background pixels in the neighborhood of test pixel #1. If $K_{TB}$ equals the specific number, the comparator 132 alerts the voter 134 which then adds a "vote" to the "vote" count associated with the nearby pixel, keeping a separate running "vote" count for each pixel. Otherwise, the detector device for the embodiments employing polychromatic x-rays is the same as previously described for the embodiment employing monoenergetic x-rays.

Structure and Operation of a Particular Embodiment

The inspection system is an x-ray instrumentation system designed to inspect baggage for the presence of threatening substances and materials.

The system in FIG. 11 consists of a pulsed dual-energy x-ray source 91 emitting a fan beam 91a of x-rays which penetrates the item to be inspected 91b; a rotating filter drum and timing wheel 92 to filter the fan-shaped beam of x-rays at two energy bands of x-rays synchronized to the x-ray source 91; 2 calibration shuttles 93, 94 which contain materials used to calibrate and check the operation of the machine; a conveyor belt 95 or other means to scan the baggage past the x-ray beam; an array of x-ray detectors 96 which provide calibrated values of x-ray attenuations at all points of the scanned item to a signal and image processing computer 97 which processes the detector data to compute the probability and location of threat substances to be detected in the image, an alarm 98 which is triggered if the processed image yields a value which exceeds a certain threat threshold, and a display 99 which displays the x-ray attenuation image with superimposed color indication threat substance is present.

The system also includes a means of control constituted by an operator's control console 100, which provides control of the inspection system and its operation, a footpad switch 110 to sense the operator's presence, and various other features provided to facilitate the system's operation in an industrial or security environment.

X-ray Source

Referring to FIG. 12, the inspection system consists of an x-ray source 120, capable of producing pulsed beams of x-rays 121, which alternate between high energy bands and low energy bands of x-rays. This x-ray source consists of a high voltage transformer 122 with a nominal primary voltage of 100 volts and having two secondaries of 70 kV each, connected to an arrangement of high voltage diodes 123. These diodes are connected to an x-ray generating tube 124 such that on one set of alternate half cycles, both transformer secondaries (140 kV) are connected across the x-ray tube, and on the other set, only one of the secondaries (70 kV) is placed across the x-ray generating tube. The voltage developed across the x-ray generating tube is monitored by a resistive voltage divider circuit 127 by the x-ray source controller circuit 126 and the primary voltage is adjusted accordingly.

All the above components, i.e., the x-ray generating tube 124, the transformer 122, the diodes 123, and monitoring circuits 125, 126, 127 are mounted within tank 336 and immersed in insulating oil. The tube current during the low energy pulse of x-rays is also monitored by means of resistive shunt 125 and the value used by x-ray controller circuit 126 to adjust the tube filament voltage via filament transformer 128 to maintain the x-ray tube current at a constant value.

X-ray Controller Board

The x-ray controller board 126 receives 117 VAC nominal at 50 or 60 Hz, timing, control, and interlock signals from the System Interface Board (FIG. 17, 160), tube voltage and current feedback from monitoring circuits connected to the x-ray tube source, and supplies energizing voltages to the HV transformer 122 and to the tube filament transformer 128 to effect an accurate series of 70 kVP and 140 kVP x-ray pulses at a uniform dose, timing, and energy. In addition, the x-ray controller provides status and readback signals to the system host computer (FIG. 17, 164).

Calibration Shuttles

The calibration shuttles (FIGS. 13, 93, 94) are 2 assemblies placed next to the x-ray source tank 336 in the x-ray beam 91a to allow the programmable insertion of background and detected materials or foreground simulants into the beam. The purpose of the calibration shuttles is two-fold, to check the operation of the machine as each sample of known materials should measure within certain specified limits, and to monitor the long term drifts of the instrument and to provide data used to generate the $K_{MAT}$ lookup table used in the detection algorithm.

One shuttle (FIG. 13b), the background material shuttle 93, contains an assortment of background materials 330–333, with several different thicknesses of each, ranging from low-Z materials (plastics) to high-Z materials (metals). The other shuttle (FIG. 13c), the detected material shuttle 94, contains materials 341–344 which are accurate simulants of the desired substances to be detected.

Each shuttle consists of strips 330–333 and 341–344 with several thicknesses of specific materials (FIG. 13d showing an endwise view of a strip) mounted on a frame interleaved with empty areas 335 which are the normal position, connected mechanically via a belt 345, or as presently preferred, a lead screw, to a stepper motor 334 which allows the shuttle position to be changed by the controlling computer. An idler wheel 340 provides mechanical stability.

During a calibration cycle, a procedure performed when there is nothing in the beam (e.g., between bags), a certain thickness of specific threat material is inserted into the beam along with a certain thickness of a specific background material, and the value stored, until all combinations of background and threat materials have been so measured with enough samples to be statistically significant.

Filter Drum and Timing Wheel

A motor driven spinning drum of plexiglas (FIG. 14a, 92) or other plastic is lined with strips of lead 151 and brass 152 aligned along the long axis (cross-section view given in FIG. 14b) and inserted into the x-ray beam to effect a filter for the high x-ray pulse (140 kVP) and to effect a shutter with lead strips for the transition area between high and low energy pulses to effectively stop the beam for dark current compensation during beam transitions.

A timing wheel 153 in FIGS. 14a and 14b, consisting of a disk with holes arrayed around the perimeter and mechanically coupled to the filter drum, acts in conjunction with 2 optical interrupter circuits 154 to issue low beam and high beam timing pulses to the system interface board (FIG. 17., 160), and ultimately to the x-ray source and to the detector array electronics.

One of the timing wheel holes 155 is a double hole providing a double pulse to the system interface board thus providing the system with a reference to a specific set of filter drum strips for possible calibration of system timing to individual filter strips.

This assembly is driven from a line-synchronous motor 156 and thus all timing pulses and x-ray pulses are synchronized to line frequency providing a measure of line-frequency rejection of system errors.

Conveyor

A motorized conveyor (FIG. 15, 95) is provided which moves the baggage (FIG. 11, 91b) or items to be inspected at a constant rate past the x-ray beam (FIG. 11, 91a) and detector array 96 and delivers the inspected baggage to a pickup area on the outlet side of the machine.

This conveyor consists of a powered roller 180 mounted on the outlet side of the machine, an idle roller 181 at the inlet side, and a belt 182, mounted as a continuous loop between the two rollers.

Control is provided at the operator console to start and stop the conveyor as well as set its direction (forward and reverse).

Baggage Detection Photocells

Two sets of light source-photocell combinations 183, 184 are provided to sense the position of the baggage at two places along the belt, the first position encountered as the baggage enters the x-ray tunnel (about 15" from the beam) and the other set an equal distance on the other side of the beam 185.

The 2 levels of photocell item detectors allow internal sequencing of the operation of the machine for air point calibration and calibration shuttle sequencing as well as times required for beam turn-on.

Detector

Referring to FIG. 16a, the detector array 170 is an L-shaped arrangement of 960 detector elements and is designed to detect a fan beam of x-rays (FIG. 11, 91a) at high and low energy bands efficiently and rapidly with as few errors, as little noise, as possible. Dynamic and static calibration is done to provide the optimum level of accuracy.

The detector array provides a digitized stream of values representing the high and low x-ray band detection values as well as dark current values for each detector at a rate consistent with 240 x-ray flux values and 240 dark current values for each detector every second, at 60 Hz. (The system runs correspondingly slower at 50 Hz delivering 200 samples per second and 200 dark current values per second.) The detector provides these values over a cable to the Detector Interface Board (FIG. 17, 161).

The Detector Interface Board computes dark current compensation and air point subtraction algorithms and provides a stream of equalized logarithmic values to the transputer array (FIG. 17, 162).

The algorithm involved in transforming the detector array output values into values sent to the transputer array is detailed in *Dark current and Air point compensation*, below.

Photodiodes and Scintillators

Each detector consists of a large area photodiode (FIG. 16a, 172), with a scintillating material 173 glued over its active area with an optically transparent epoxy. When exposed to incident x-ray radiation 174, the scintillating material converts some of the x-rays to visible photons, which are then converted to small electric currents by the photodiodes.

It is important that the scintillating material exhibit good efficiencies at both energy bands with especially high efficiency at the low energy band of x-rays. It must also exhibit very little 'afterglow' which must decay very rapidly after the removal of the x-ray flux.

The photodiodes are custom-made arrays, 32 per array, optimized for active area and low noise characteristics.

Electronics

The detector electronics (FIG. 16b, 178, 179) are designed to amplify the nano-ampere signal currents from the photodiodes, provide a small reverse bias to each diode in the array, and integrate and amplify the resulting currents to provide a voltage to be digitized by the converter board. It is necessary that the electronics contribute as little noise as possible to the resulting signal.

Preamp/Mux Board

The Preamp/Mux board assembly 178 consists of 2 printed circuit boards mounted together with an intervening shield board to provide signal isolation and x-ray shielding. Each board assembly contains 64 channels of a dual integrating functional block, one half of the integrators being for high energy beams and one half of the integrators being for low energy beams. This block also provides a small reverse bias to each photodiode in the array.

The signal output from the Preamp board 175 is sent to the Multiplexor board 177 and distributed, 8 signals at a time via 8 analog busses, to the Analog-to-digital (A/D) conversion board 179. The timing control for the Mux board is received from the A/D board.

A/D board

The A/D board 179 receives timing information from the detector interface board (FIG. 17, 161), mounted in a VME card cage and backplane, and distributes timing information to the array of detector Preamp/Mux boards 178. It then receives analog voltage information from these modules, 8 lines at a time, and converts these values to ranged 12 bit digital numbers. These values are then output to the detector interface board 161 for dark current and air point compensation.

The A/D board 179 also returns voltage status information to the environmental monitoring board in the VME card cage.

System Interface Electronics

The System interface electronics (FIG. 17, 160, 161, 163) consists of 3 VME standard size cards mounted in the VME card cage along with the host computer 164 and its options, and the transputer array 162. These boards perform the majority of the inspection system hardware interface.

Detector Interface

The Detector Interface board 161 receives a stream of digital values from the detector in response to timing and control information provided to the detector by this board.

This board also performs dynamic, value by value, dark current correction and air point compensation, and optionally dynamic filter drum calibration, (see *Dark current and Air point compensation*, below).

The detector interface board also does logarithmic conversion of the data and finally sends the data to the transputer array via a transputer link 165.

System Interface

The system interface board 160 receives timing information for the filter drum timing wheel and issues customized timing pulses based on a synchronized crystal controlled clock signal and various state-machine based circuits. These pulses are then sent to the x-ray controller board and to the detector interface board.

This board also receives interlock signals, from both mechanical and electrical interlocks in the system, and distributes interlock and control information to the x-ray controller.

The system interface board controls the operation of the stepper motor controlled calibration shuttles.

Environmental Interface

The Environmental Interface board 163 monitors all DC and AC voltages as well as certain temperatures at various places throughout the machine. If the monitored parameters exceed certain programmable limits, warnings are issued to the operator and the operation of the machine can be inhibited.

This board also provides operator console interface and supplies power and output signals to the console to light switches or sound alarms, receives information concerning switch closures, and data from the console mounted touch panel area.

Operator Console

The operator console 166 is the primary means of system control for the operator. It contains switches that enable power and x-rays for the machine, switches that control the action of the conveyor (stop, start, direction), switches that control the operation of the display to modify system display modes and contrast adjustment, and a touch panel which provides a method of moving a cursor or 'zoom window' around a display screen. It also holds an alarm annunciator to provide audible feedback signals to the operator.

The switch array includes switches that are 'deadfront' when inactive or unavailable to simplify the operation and appearance to an unskilled operator. These switches may provide a variable backlit intensity to signal available options versus options currently in effect.

Computer System

The computer system (FIG. 17) is structured as a VME backplane containing a Host computer 164, which has full access to all other cards mounted in the VME backplane, various peripheral cards 167 which provide disk storage, computer network communications, etc., and an array of VME cards 162 which contain an independent computer subsystem consisting of numerous computers, known as Transputers manufactured by Inmos/Thomson, interconnected so as to form a large network of 10 or more transputers depending upon the application. This transputer array is dedicated to processing the detector array data received from the detector interface card to primarily detect specific substances (threat materials) in random baggage of unknown composition, and to produce an image on a high quality color computer monitor screen 168.

Host and Peripherals

The host computer system 164 consists of a commercially available processor board based on the Intel 80386 CPU and may optionally include peripheral circuitry such as 4 MBytes of RAM, math co-processor, and a full array of communication ports.

One of the peripheral boards in this group is the mass storage peripheral card which provides a ruggedized 40 Mbyte hard disk, a 3½ inch microfloppy disk, and SCSI interface for future disk expansion.

All program code used by the host computer group as well as the code used on the transputer array is stored on the 40 Mbyte hard disk and downloaded into operating RAM at system turn-on.

The Host has the responsibility for bootstrapping all relevant code to the respective computing elements, causing the system to respond to commands from the operator via the operator console, continuously checking all system voltages and temperatures by reading the environmental monitor board, and providing operator warning messages via the system annunciators or the operators display screen.

Transputers

The Transputer array 162 is a series of interconnected VME cards which provide the ability to contain an arbitrary array of transputer modules, with differing combinations of transputer types (16, 32 bit, floating point) and external memory capacity. This array of transputers can be programmably interconnected to form networks of transputers with an aggregate computing capacity of over 300 Mips (Million Instructions Per Second). The algorithm employed to detect specific threat materials in baggage is computationally intensive and requires a computing element of this performance or better to be able to image the data in near real time.

Each Transputer communicates with its neighbors in the network via 4 built-in communication links with direct memory access capability. The electrical and bit protocol of these links is standardized among all transputer types, and allows easy, transparent communication from one transputer to another, one sender and one receiver per link (communication is bidirectional). The first transputer in the transputer array receives data via a transputer link from the detector interface card. The link interface is provided on an integrated circuit, Inmos/Thomson C012, for interconnection with non-transputer circuitry.

The final transputer in the network shares memory with a high performance graphics adapter circuit, G300 from Inmos/Thomson. This circuit provides an image on the monitor from data stored in memory providing up to 256 colors on a 1024 by 1280 computer monitor. This circuit also provides up to 64 shades of grey for high quality x-ray attenuation images.

The intervening network of transputers implement all processing required to implement the image detection algorithm detailed below in near real time. Certain combinations of image data may involve an extraordinary or unusual amount of processing. A memory buffer is provided at the input side of the transputer array to accommodate differing detector and image processing data rates.

Display System

The display subsystem 168 incorporates a high quality computer display monitor which can provide a normal grey-scale x-ray image with color overlays to highlight differing kind of threats and to provide color and enhanced black and white images. Current resolutions contemplated would be 960 by 1280 pixels.

An optional composite video convertor can be included which converts the RGB color monitor signals to composite video for recording images on video tape.

A color graphics printer may be included to allow for paper copies of on-screen images.

Processing and Mode Algorithms

Figure 8:
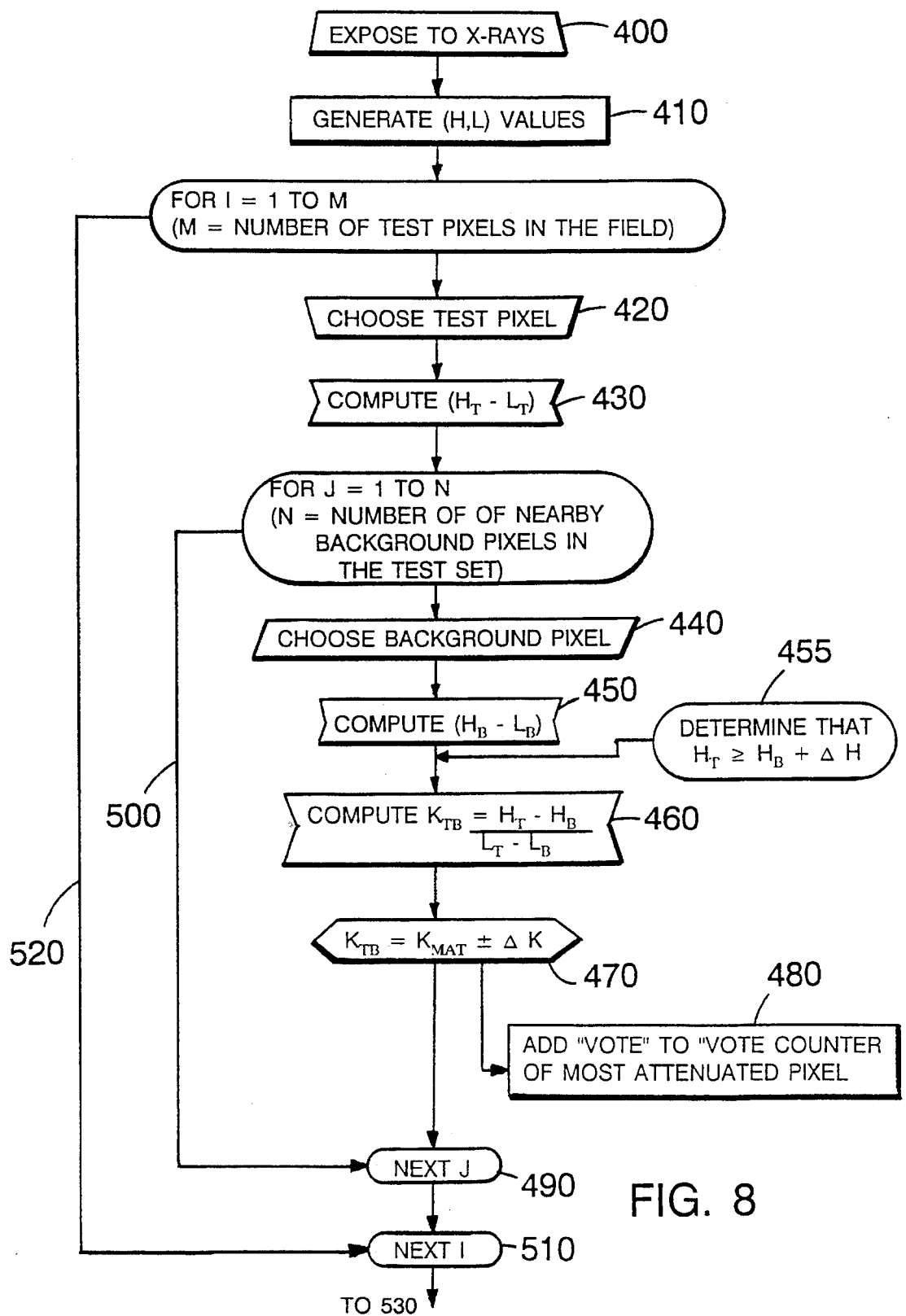
FIGS. 8 and 8(a) show a more detailed flow diagram for detection algorithms.
Figure 8A:
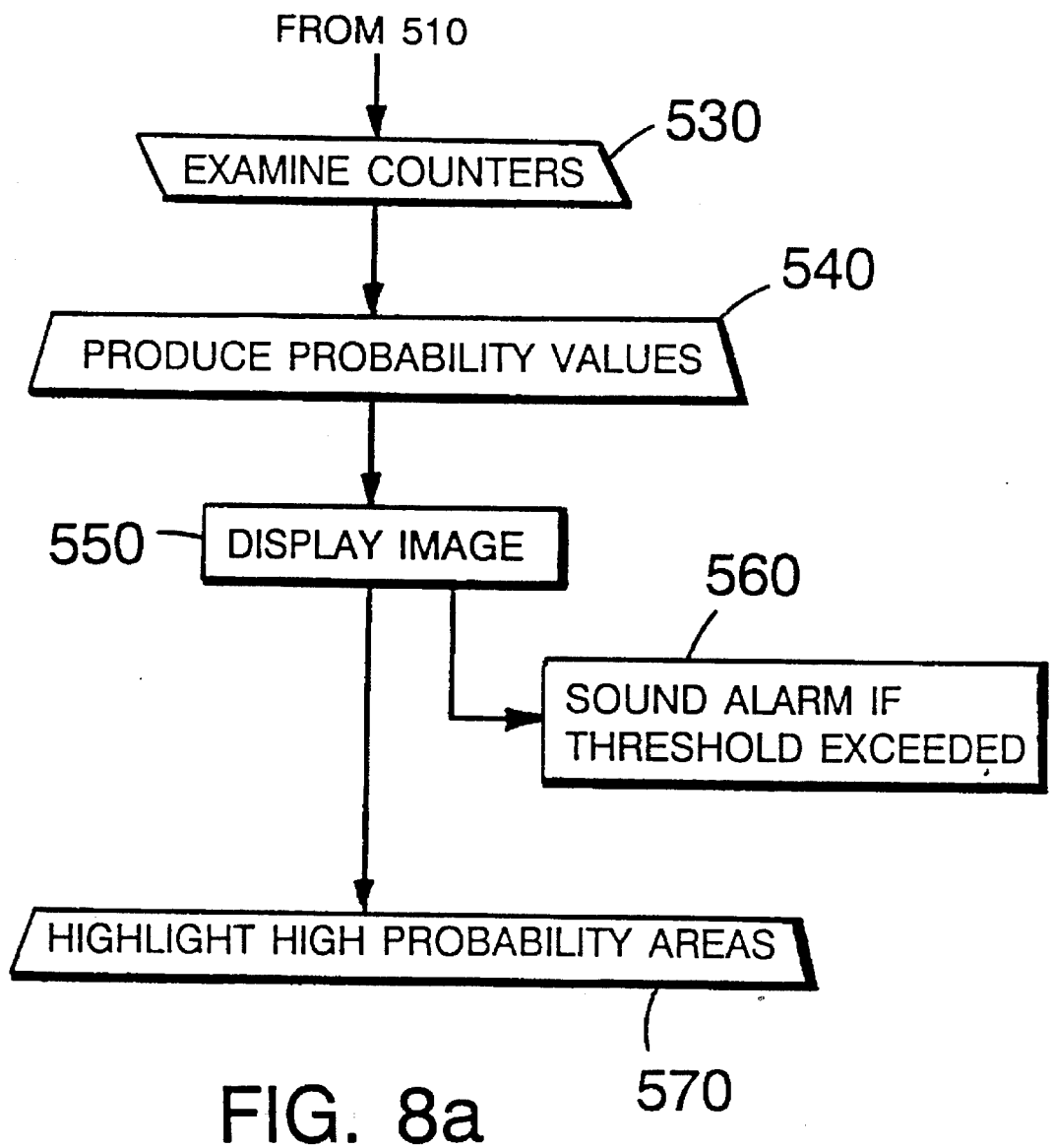

The following algorithms are suitable for detection of specific items in baggage. Extensive non-linear averaging of pixel data in the image is performed to increase accuracy of the detection algorithm. Refer to FIG. 8.

Detection Algorithm

1. Take (H,L) data (400,410) for substantially all pixels in the image or object to be examined where H and L refer to the logarithm of the x-ray attenuation at the high and low energy x-ray bands, respectively.

2. Choose a pixel to be tested taken to be a test pixel (420).

3. Compute the value (430) of $(H_T, L_T)$ for this test pixel which may involve 1 or 2 dimensional filtering, averaging, or other processing of pixel data.

4. Choose a nearby pixel to be a candidate background pixel taken to be a background pixel (440).

5. Compute the value (450) of $(H_B, L_B)$ for this background pixel which may involve 1 or 2 dimensional filtering, averaging, or other processing of pixel data, and determine (455) that $H_T$ is greater than or equal to $H_B$ by an amount $\Delta H$ related to the accuracy of the system and the nature of the material to be detected.

6. Compute the value (460):

$$K_{TB}=(H_T-H_B)/(L_T-L_B)$$

7. In the case of mono-energetic x-ray band spectra, compare this value of $K_{TB}$ to the value of $K_{MAT}$ (470), where this value is equal to $$K_{MAT}=\mu_H/\mu_L$$

where $\mu_H$ and $\mu_L$ are the attenuation coefficients of a specific material in the high and low bands of x-rays respectively, or, In the case of non-monoenergetic or polychromatic x-ray band spectra, this value is equal to $$K_{MAT}=\frac{\mu_H(H_T,H_B,L_T,L_B)}{\mu_L(H_T,H_B,L_T,L_B)}$$

where $\mu_H$, $\mu_L$ are functions of the specific material to be detected as well as the attenuation values of both the test pixel and the background pixel.

If this value, $K_{TB}$, is within a selected window of values of $K_{MAT}$, then increment a counter (480) corresponding to the most attenuated pixel of the pair, test and background pixels, where each pixel in the image has a corresponding counter stored in memory.

10. Choose another background pixel (490), which may be the next pixel in a square neighborhood of pixels surrounding the test pixel, or by use of a different algorithm and, 11. Repeat steps 5 through 10 until a substantial number of background pixels have been examined (500).

12. Choose another test pixel (510), which may be the next pixel in a line of pixels in the image, or by use of a different algorithm and, 13. Repeat steps 3 through 12 until substantially all chosen pixels have been tested in the image (520).

14. Examine the pixel counter data (530), and, for all pixels with counts greater than or equal to a selected threshold value, process the counter data and the pixel data in the image to produce values for each pixel that indicate the relative probability that the pixel under test is a match to a specific material (540).

15. Display all pixels comprising a standard x-ray attenuation intensity image (550) which may use both H and L data to produce the image on the display screen.

16. Process all pixels that have a probability greater than a selected threshold of a match to the specific material in a way that produces a single value for the image, called threat presence value. If this value exceeds the threshold then an alarm, the threat present alarm is triggered (560), and, 17. Display all pixels that have a probability greater than or equal to a selected threshold of a match to the specific material in a way that highlights (570) these specific pixels in the x-ray image (e.g., color).

Dark Current and Air Point Compensation

Periodically (once per item to be inspected) take a sample of the x-ray detector output which is proportional to incident x-ray flux, at both high and low energy bands, with nothing in the beam (except the intervening air) and store these values ($\chi_{AirH}$, $\chi_{AirL}$).

Periodically (once per x-ray pulse) take a sample of the detector output with no x-ray flux (lead in the beam) and store this value ($\chi_{Dark}$).

Use these values, $\chi_{AirH}$, $\chi_{AirL}$, $\chi_{Dark}$, and the output value of the detector with an item of interest in the beam, $\chi_{SampleH}$, $\chi_{SampleL}$ at high and low energy bands, and calculate the value of the log attenuation of that sample relative to air and dark current corrected as:

$$H = k\, \text{Log}_{10}([\chi_{AirH} - \chi_{Dark}]/[\chi_{SampleH} - \chi_{Dark}]) \quad L = k\, \text{Log}_{10}([\chi_{AirL} - \chi_{Dark}]/[\chi_{SampleL} - \chi_{Dark}])$$

where k=counts/decade.

Special Calibration and Procedures Threat Material Calibration

Periodically, e.g. by use of the shuttle shown in FIG. 13, insert a calibration material into the beam which may consist of a number of specific foreground materials or simulants as well as a number of background materials, chosen such that the effective atomic number 'Z' of the background materials span a range of low-Z (plastics) to high-Z (metals) in such a way that each specific material is sampled over all the background materials as well as air.

Store the measured value and accumulate (average) the data until enough samples have been accumulated of each combination of specific (threat) and background materials to be statistically significant.

When enough samples have been accumulated, use these values to determine $K_{MAT}$ for the specific material (monoenergetic beams), or to regenerate the $K_{MAT}$ lookup table (non-monoenergetic or polychromatic case).

There are two shuttles in the machine that can insert various calibration materials into the fan beam of x-rays. One of these shuttles is called the background materials shuttle, the other is the threat substances shuttle.

The operation of these shuttles is controlled by the operation of 2 stepper motors which, in turn, are driven via the system interface board by the host software.

These shuttles contain strips of materials interspersed with air gaps. Each material is represented by 3 thicknesses of said material, to allow measurement of several thicknesses of each material. The air gap is positioned in the beam during normal baggage inspection.

These materials are of various types. The background materials shuttle contains strips of 5 background materials, currently planned is iron (~1 mm/step), aluminum (~4 mm/step), lexan or lucite (~10 mm/step), melamine resin (~10 mm/step), and noryl (~10 mm/step).

The threat substance materials will be fabricated from a combination of epoxy plastic and aluminum powder, in a proportion that simulates various threat materials in x-ray attenuation. These proportions will be determined experimentally. The result is a hard plastic-like material which can be machined into a series of stepped wedges, see FIG. 13(*d*).

This arrangement allows the system to insert a choice of background material of a particular thickness and a choice of threat substance of a particular thickness in the x-ray beam enabling measurements of these materials during a calibration cycle (no baggage in beam) or between successive bags on the conveyor.

This allows the system to take a series of measurements that describe a matrix of background and substance materials of various thickness. For example if the background shuttle contains 5 substances of 3 thicknesses each (plus air) and the threat substance shuttle contains 5 substances of 3 thicknesses each, then a total of ((3*5)+1)*(15) or a total of 240 separate combinations of background and threat substance materials can be measured.

The high and low energy beam attenuations are known for these 240 combinations, either due to the mechanical thicknesses and tolerances of these known materials or due to factory calibration values stored for each of these combinations in the machine.

These values can therefore be used to verify calibrated operation of the machine by checking the values stored or calculated against the values measured during a verification cycle.

The measurements of the shuttle materials may be averaged in order to increase the accuracy of the data. A likely number of samples averaged together may range from as few as 10 to as many as 1000 samples per measurement per detector element.

These measurements can be used to calibrate the system by generating correction constants, that, when applied to the data from the detector array, serve to correct the data to compensate for long-term drift of the system due to aging or other unknown phenomena.

Experimental Demonstration

A series of measurements of various objects were made using the Hologic QDR 1000 dual energy x-ray bone densitometer adapted with custom software. These objects consisted of stepped wedges of various materials that approximate the attenuation characteristics of materials of interest, as well as sheets of these and other materials.

The data taken consisted of a series of high and low energy x-ray attenuation values (H,L), one set per step in the wedges. Many samples of each step were taken and averaged in order to lower the noise in each measurement which is due to x-ray quantum noise as well as electronic noise. The value of the x-ray flux in air (no object in the beam) was taken at each step in the wedge in order to accurately characterize the attenuation of the incident x-ray flux by the measured object despite time-related drifts of the x-ray data caused by inaccuracies in the Hologic densitometer.

Two types of equations were derived from these measurements. One set of equations was developed that described the path in a mathematical space whose axes are the high energy beam attenuation and the low energy beam attenuation, hereafter referred to as HL space, of multiple thicknesses of the same material, where the type of material is characterized by a number called $K_m$. $K_m$ is the ratio of high energy beam attenuation H to low energy beam attenuation L with a thin piece of a material inserted into the x-ray beam and nothing else (i.e. the beam is unfiltered by overlying substances). With monochromatic x-ray beams this path would be a straight line, but in the polychromatic case, this line is a curve because of the beam 'hardening' effects. This path is characterized by computing the expected low energy beam attenuation L, given the high energy beam attenuation H and $K_m$ of the material of interest. The value of the high energy beam H is used as an independent variable here and elsewhere because its value is primarily due to Compton effect interactions and has very little energy dependence and is basically proportional to mass. The low energy beam interacts primarily due to the photoelectric effect and as such is proportional to energy and mass.

Another set of equations were developed that described the "$K_{ref}$" or the ratio H/L of high energy to low energy attenuation due to the insertion of a particular substance over various types of other materials. Here, the particular substance was characterized by two numbers, $K_o$, which represents the ratio of high energy beam attenuation to low energy beam attenuation with nothing else in the path (unfiltered beam) and $K_L$, which is the ratio of high energy beam attenuation to low energy beam attenuation over heavily filtering backgrounds. Note that $K_o$ and $K_m$ are identical for a given substance. Here, $K_m$ refers specifically to background materials, and $K_o$ refers to a substance of interest (bomb substance).

$K_L$ cannot be directly measured, however, being the value of K after essentially infinite filtering. Instead a series of measurements are made of the high and low beam attenuation of a substance over background materials, which are then fit to a function of $K_o$ (measured) and $K_L$, resulting in a number for $K_L$. The $K_{ref}$ for any particular substance varies depending on what, and how much, 'background' material is also in the beam, i.e., it depends on the level of the incident x-ray beam filtering. $K_{ref}$ for any substance can thus be described as a function of the high energy beam attenuation (of the background material), the $K_m$ of the background material, and $K_o$ and $K_L$ for the substance of interest.

This set of equations and the values of the per substance constants were all derived empirically from measurements on the Hologic densitometer. The form of the equations was experimentally determined by observing the data and using a commercial statistics package to do the non-linear regressions. In some cases data was taken from actual x-ray images of baggage with bomb materials inserted (also taken on the Hologic machine) and used to determine some parameters of the fitted equations.

To convert these equations to a $K_{ref}$ lookup table as a function of measured high energy and low energy beam attenuations, a two pass process was used given schematically in FIG. 10. In the first pass, a value of high beam attenuation H is chosen (700). Then $K_{ref}$ for these values of H, $K_o$ for the substance of interest, and $K_m$ for aluminum (0.26) was calculated (710). This will be the highest $K_{ref}$ for the substance of interest (most heavily filtered). Then $K_{ref}$ for the same values of H, $K_o$, and $K_m$ for plastic (0.8) was calculated (710). This will be the lowest $K_{ref}$ for the substance of interest (at these values of high energy beam attenuation). Then 1% changes (4% if high energy beam attenuation is greater than 800) in $K_{ref}$ are incremented between these two values of $K_{ref}$ (720, 730). At each iteration, the corresponding value of the low beam energy attenuation L is calculated, and the difference from the last value of low beam attenuation is noted (740). If this difference value is less than the last difference value (750), then it is stored (760). After all values of $K_{ref}$ between the low and high values of $K_{ref}$ have been calculated, the smallest resulting increment of low beam attenuation is available.

This value of low beam attenuation difference is rounded down to the nearest number that is a power of 2 (785), and this value used to generate the second pass and the actual lookup table. The second pass iterates on low beam attenuation (790), from the lowest value (over the highest $K_m$) to the highest value (lowest $K_m$) resulting in a series of equally-spaced (in low beam attenuation value) entries in a table for a particular value of high beam attenuation H, each entry containing the calculated $K_{ref}$ for a particular substance (800). The spacing between entries is a power of 2 to improve computational efficiency, and the value of $K_{ref}$ from entry to entry is guaranteed to be less than 1%. When the table is finished it will have been iterated for all desired values of high energy beam attenuation, currently 1 to 2000, which, at 819 values per decade of attenuation, spans approximately 2½ decades of attenuation. Beyond this value of attenuation, no detection is performed in the image because noise degrades the signals too much for accurate detection.

This table can be used therefore, to detect bomb substances by comparing the $K_{ref}$ of an object in an image (i.e. its incremental k, determined by the equation $k=(H_{bmb}-H_{bg})/(L_{bmb}-L_{bg})$) to the value in the lookup table at the (H,L) coordinates of the background pixel.

The method so far described can be improved somewhat. The equations developed so far to describe $K_{ref}$ in HL space are modeled on thin pieces of the specific substance to be detected, i.e. filtering due to a thick piece of the detected substance causes the $K_{ref}$ approximation to be less accurate. Essentially this comes from treating the path that the specific substance describes in the HL space, when placed over a background substance, as a straight line. We know from the data that this path is really a curved line, with the most rapidly changing part of the curve nearest to air, i.e. in lightly filtered beams. This means that the detection algorithm stated above can be improved, especially when inspecting thick bomb materials, and thin bags rather than thick bags.

In order to improve the detection algorithm in these situations, the $K_{ref}$ value in the lookup table at the bomb (H,L) coordinates is also read, not just the value at the background (H,L) coordinates. The value of k (defined above) is then compared to $0.8(K_{ref}^{background}$ from table)$+ 0.2(K_{ref}^{bomb+background}$ from table). In order to improve the detection, curve fits were done using data from images and this equation and were used to generate new tables of $K_{ref}$ values. The values (0.8,0.2) were arrived at with experimentation and were designed to improve the detection in several images with little or no background materials near the bomb material.

This method is valid for background materials with Z's between plastic and aluminum. With higher Z materials (lower $K_m$) such as iron, the set of equations produce less valid values for the paths and the $K_{ref}$s.

The equation that predicts paths of varying thicknesses of substances in the HL space has known inadequacies in predicting the paths of actual substances with errors sometimes as great as 40 or 50 in low energy beam attenuation values at 819 values per decade of attenuation.

Detailed Explanation of Appendix ALGO.DOC
(lookup table generation and detection)

The appendix, ALGO.DOC, hereby incorporated by reference, contains excerpts from the actual 'C' code used to generate the lookup tables and do the detection in the image. These are code fragments but should describe all relevant algorithms.

Three constants are defined, MIN_HI, MAX_HI and HI_INDEX, which define the valid range of the generated table and lookup table granularity.

A specific flag is set (i.e. 'C4') to direct generation for a specific bomb material.

Following this are defined the derived parameter values for each type of material. Six 'z' parameters are defined to be used for all materials, followed by five material-specific parameters, c1, c2, c5, K0, and KL.

Five functions are then defined, bh(km), alpha(km), beta(km), newlow(h,km), and $K_{ref}$(Hi,km, k0). The function $K_{ref}$ (which uses bh) calculates the value of kref for a particular substance over a particular background of a given attenuation. The function newlow (which uses alpha and beta) calculates the corresponding low energy beam attenuation value over a particular type of background material with a particular value of high energy beam attenuation (thus describing a 'path' in HL space for various thickness of a given substance).

Two functions are then defined that iterate on the above functions to find the value for parameters when no specific equation for that relationship exists.

For example, no explicit function has been described to provide a value for km given high beam attenuation, K0 of a specific material and a particular kref for that substance (over a background of the unknown km). The function find_Km iterates on the function $K_{ref}$ to approximate a value for km that satisfies the above parameters.

Similarly the function find Km_low approximates the desired value of km given a value of high and low energy beam attenuations, i.e. the km for a background material whose 'path' or locus of points in HL space intersects the given value of hi and low attenuations.

Next is the fragment that describes the main algorithm which generates the substance kref lookup table. ('create the histogram')

A set of table entries for each value of high energy beam attenuation are generated each time through the main loop which increments the variable 'hint'. The loop body is executed for each value of high beam attenuation, and for a particular set of c1, c2, c5, K0, and KL.

These parameters are used to generate the values for hi_kref and lo_kref which are the kref values for a particular substance with a specific K0 (and KL), over aluminum (km=0.29) and plastic (km=0.8) respectively. These end values of kref (at this value of high beam attenuation) are used to define a loop which calculates the value of the low beam attenuations at successive 1% increments of kref. 4% increments are used if the value of high beam attenuation exceeds a value of 800. Inside this loop the smallest increment of low beam attenuation resulting from these increments is stored. This value for the smallest increment of low beam attenuation required to insure 1% or less steps in kref, is rounded down to a power of 2 ('tdiffl') and is used as the increment in a second loop.

This second loop uses the current value of high beam attenuation and generates a series of values of low beam attenuations. These values of low beam attenuations range between the kref endpoints with an increment of 'tdiffl' low beam attenuation values to generate the kref lookup table. This table thus contains entries spaced at periodic gridpoints in HL space (i.e. at specific values of High and Low beam attenuations).

For each value of high beam attenuation, a header containing the data specific to this set of entries is stored. This header contains the first low value for which data is stored ('MIN_LO'), the scale factor ('LO_SCALE'=tdiffl), and the largest value of low for which data is stored ('MAX_LO'). This header data is followed by the actual values for $K_{ref}$ for this set of entries (corresponding to a particular high energy beam attenuation value).

Finally, the number of kref 'bins' is output to the console to provide a measure of storage required to store the lookup table.

The detection algorithm is then documented in the procedure DoBox.

Detection Algorithm Using the Generated Lookup Table

The procedure DoBox, examines the high and low beam attenuation data and produces a value for each pixel at the center of a square neighborhood of pixels ('box') which is a measure of the 'hit' or 'vote' count of this center pixel measured against all pixels in this neighborhood. This 'hit' or 'vote' count is a measure of the probability that this pixel represents an unknown amount of a particular substance over a 'background' material represented by a nearby pixel.

Each invocation of DoBox represents the calculations required for a single center pixel.

The function, AveragePixel, is called to perform a 2-d averaging for all like pixels in a neighborhood of pixels to reduce noise.

If the averaged value of this pixel exceeds 2000 then it is deemed too opaque to examine.

A threshold is calculated that sets the minimum difference in high beam attenuations between pixels that enables the detection algorithm ('mindiff').

The main loop of the detection algorithm is entered. If any pixel is on an edge ('pxl->sobel') it is not examined.

Each pixel to be compared to the center pixel is then averaged (with like pixels in the neighborhood) and thresholded in high and low beam values. If the threshold is exceeded, kref at both the center and the test pixels are retreived from the lookup table and are tested in the equation 'krefavg=(kreflo*0.8)+(0.2*krefhi)' where kreflo is the least attenuated of the test and center pixels and krefhi the most attenuated of the two pixels.

If the resulting value of krefavg is within a window of values of "Diffk" then a count for the center pixel is incremented ('midpxl->histval++'). This value is then stored and is a measure of the probability that the center pixel represents a specific substance over a nearby background pixel. These threshold values, MinThreshold and MaxThreshold, can be set in the command line when the detection algorithm is invoked or else defaults to −0.01, 0.01 if not otherwise specified.

Detection Algorithm Using 'P-Value' Lookup Table

An alternative algorithmic embodiment involves a 'p-value' lookup table. This method creates a series of 'paths' or trajectories that describe various thicknesses of bomb material over various thicknesses of 'basis' materials.

This is potentially much more accurate since various thicknesses of bomb materials are correctly modeled and the values produced are valid over the entire basis set, i.e. boron to iron.

The detection algorithm detailed above and in the appendix is modified to use the p-value lookup table by replacing the kref lookup with a p-value lookup for both the test pixel and the center pixel. These p-values are compared, and if they are within a window of values of each other, i.e. the difference between the two p-values is 0 or a small number, such as 5, then the two pixels are related by an overlying bomb substance.

In preferred embodiments, an edge finding or gradient evaluating algorithm is applied to the data for the H image (or, alternatively, the L image) and a P image formed from the p-value data. An edge that showed up in the H image data but not in the P image data would be indicative of the presence of the specific substance of interest. A convenient measure characterizing the presence of an edge of the specific substance of interest in the H image and its absence in the P image is given by the ratio of the gradient value of a pixel in the H image to the gradient value of that pixel in the P image, with the respective gradient values provided by an edge finding or gradient evaluating algorithm. For example, the Sobel value for a pixel in the H image is compared to the Sobel value for that pixel in the P image.

A preferred algorithm using this detection technique is given schematically in FIG. 19. The first step (2000) is to determine H and L values in the image. Optionally, substances of less interest, such as metals when plastic explosives are being detected, can be filtered out and removed from the image, preferably by using p-value data for the substances of less interest. The next step (2010) is to apply an edge finding or gradient evaluating operator such as the Sobel operator to the H image, for example, generating Sobel values $H_{Sobel}$ for all pixels. Then (2020) the image is pruned to remove those pixels whose Sobel values $H_{Sobel}$ are below a given threshold. Following this (2030) p-values are determined for the remaining pixels with Sobel values $H_{Sobel}$ above the given threshold. The next step (2035) is to apply the Sobel operator to the resulting P image formed using the p-values for the remaining pixels, generating Sobel values $P_{Sobel}$ for the remaining pixels. Then (2040) the ratio $H_{Sobel}/P_{Sobel}$ is calculated for the remaining pixels. Optionally (2050) the ratio $H_{Sobel}/P_{Sobel}$ can be raised to a power greater than one, for example squared, to better emphasize large values of the ratio. The next step (2060) is to store the ratio $H_{Sobel}/P_{Sobel}$ on a per pixel basis. Following this (2070) a threshold on the ratio $H_{Sobel}/P_{Sobel}$ is established so that pixels having the ratio $H_{Sobel}/P_{Sobel}$ above the threshold are strongly indicative of the presence of the specific material of interest, for example a bomb. The next step (2080) is to apply a dilation algorithm using H and L values for the image. Then (2090) an alarm is sounded if a certain number of pixel values are above the threshold. An erosion algorithm is then applied (3000) to eliminate spurious noise in the image. Finally (3010) the fully processed image is displayed with areas of particular interest highlighted.

A preferred device embodying the preferred algorithm using this detection technique is given schematically in FIG. 20. An H and L value determiner 3005 determines H and L values in the image. Optionally, substances of less interest, such as metals when plastic explosives are being detected, can be filtered out and removed from the image, preferably by using p-value data for the substances of less interest. An edge finding or gradient evaluating operator such as the Sobel operator 3015 is applied to the H image, for example, generating Sobel values $H_{Sobel}$ for all pixels. Then (2020) the image is pruned to remove those pixels whose Sobel values $H_{Sobel}$ are below a given threshold. Following this (2030) p-values are determined for the remaining pixels with Sobel values $H_{Sobel}$ above the given threshold. The next step (2035) is to apply the Sobel operator to the resulting P image formed using the p-values for the remaining pixels, generating Sobel values $P_{Sobel}$ for the remaining pixels. Then (2040) the ratio $H_{Sobel}/P_{Sobel}$ is calculated for the remaining pixels. Optionally (2050) the ratio $H_{Sobel}/P_{Sobel}$ can be raised to a power greater than one, for example squared, to better emphasize large values of the ratio. The next step (2060) is to store the ratio $H_{Sobel}/P_{Sobel}$ on a per pixel basis. Following this (2070) a threshold on the ratio $H_{Sobel}/P_{Sobel}$ is established so that pixels having the ratio $H_{Sobel}/P_{Sobel}$ above the threshold are strongly indicative of the presence of the specific material of interest, for example a bomb. The next step (2080) is to apply a dilation algorithm using H and L values for the image. Then (2090) an alarm is sounded if a certain number of pixel values are above the threshold. An erosion algorithm is then applied (3000) to eliminate spurious noise in the image. Finally (3010) the fully processed image is displayed with areas of particular interest highlighted.

In other embodiments, a p-value $P_T$ is associated with the logarithmic attenuation values $(H_T, L_T)$ for a test pixel and a p-value $P_B$ is associated with the logarithmic attenuation values $(H_B, L_B)$ for a nearby background pixel, the value of $\Delta H/\Delta P$ then equals $|(H_T - H_B)/(P_T - P_B)|$. The value $\Delta H/\Delta P$ is associated with a relative probability measure for the presence of threat material at the respective pixels. Raising $\Delta H/\Delta P$ to a power q greater than unity $(\Delta H/\Delta P)^q$ serves to better emphasize extrema of the value of $\Delta H/\Delta P$. Preferably, q=2 gives a nearly optimal fit for the relative probability measure. This is a useful measure of the relative probability of two pixels being related by an overlying bomb substance.

Attenuation of x-rays in an arbitrary material can be well approximated by a decomposition into two "basis" materials. This approximation-by-decomposition result has been described by Alvarez, et al. For the purpose at hand, this decomposition is expressed in terms of a threat material and an (innocuous) overlay material. The p-value is a parameterization of the amount of overlay material. In an x-ray image, nearby pixels which differ only in attenuation due to variation in threat material thickness will have the same p-value.

We define p-values in preferred embodiments by calculating the high and low energy beam logarithmic attenuation as a function of photon energy, E, for arbitrary thicknesses of threat and overlay material. More generally, p-values can be directly associated with high and low energy beam linear attenuation values. For a monoenergetic beam the detector output is proportional to the beam strength, transmission probability, detection probability and detector response. Since the present system uses a scanning photon beam, any interaction will serve to remove the interacting photon from the beam and reduce transmission. Transmission probability is calculated from the attenuation coefficients in the beam filter and in the target material. The detector output response will depend on the nature of the detection system, the associated electronics, and on the photon energy and its direction of incidence.

Detection output due to photons of energy, E, with a target thickness, t, is then:

$$O(E,t) = kI(E)\exp(-t_F \mu_F(E)/\rho_F)\exp(-t_T \mu_T(E)/\rho_T)R_D(E) \qquad (6)$$

where $O(E,t)$=detector output
$I(E)$=beam strength before filtration
$t_F, t_T$=thickness (gm/cm$^2$) for filter and target material
$\mu_F/\rho_F$=mass attenuation coefficient for filtration (including inherent)
$\mu_T/\rho_T$=mass attenuation coefficient for target
$R_D(E)$=detector electronic output response for an incident photon of energy E. Integrating over all energies in the beam (0 to E-max), the output for a non-monoenergetic spectrum of x-ray photons is given by:

$$O(t) = \int_0^{E\text{-max}} O(E,t)dE. \quad (7)$$

The logarithmic attenuation, M, due to the target material is then $$M = -\ln[O(t)/O(0)]. \quad (8)$$

For a dual energy x-ray beam, the logarithmic attenuation for the high and low energy beams, $M_B$ and $M_L$, will differ due to the differences in their beam strength spectra $I(E)$ and the differing filtration employed for the two beams.

Beam strength arising from bremsstrahlung is proportional to (E-max–E). Additional beam strength terms arise from characteristic radiation produced from the tungsten anode. The latter effect accounts for a relatively minor fraction of the total beam strength. Computation of $M_H$ and $M_L$ is accomplished through a mathematical beam model using suitable numerical approximations, and numerical integration techniques.

For a target consisting of two separate components, such as the "threat" and "overlay" materials, the composite mass attenuation coefficient is given by $$\mu/\rho = (t_T/t)(\mu_T/\rho_T) + (t_o/t)(\mu_o/\rho_o) \quad (9)$$

where subscripts T and o denote threat and overlay respectively, and $\mu$ is the composite linear attenuation coefficient (cm$^{-1}$) and $\rho$ is the composite mass density (gm/cm$^3$). Attenuation through a chemical compound may be computed by dividing it into its elemental components. For example, a compound C given by the formula $C = A_\alpha B_\beta$, where A and B denote elements, has mass attenuation coefficient $$\mu_c/\rho_c = (\alpha M_A/M_c)(\mu_A/\rho_A) + (\beta M_B/M_c)(\mu_B/\rho_B), \quad (10)$$

where
$M_A, M_B, M_C$ = the atomic weights of elements A and B, and the molecular weight of compound C, respectively.

Using Equations (6) to (9), $M_H$ and $M_L$ logarithmic attenuation values are directly calculable for specified threat and overlay thicknesses, $t_T$ and $t_o$. By independently varying the parameters $t_T$ and $t_o$ a set of associated points $(M_H, M_L)$ may be generated. For example, with RDX as the threat material and iron as the overlay, RDX thickness was allowed to vary over 14 values ranging from 0 to 32 gm/cm$^2$ while iron thickness was independently varied over 19 values ranging from 0 to 4 gm/cm$^2$. Note that 32 gm/cm$^2$ of RDX or 4 gm/cm$^2$ of iron is sufficient to attenuate the low energy beam by a factor of roughly 3 decades (one-thousandth).

The p-value for a $(M_H, M_L)$ point is merely proportional to the value $t_o$ (except for a possible constant offset). In one representation, the conversion was chosen as: $p = 500 t_o$, where $t_o$ is the thickness of iron overlay in gm/cm$^2$. The locus of physically realizable $(M_H, M_L)$ points is bounded by curves corresponding to the lightest element, hydrogen, and the heaviest naturally occurring element, uranium. In practice, $(M_H, M_L)$ points are restricted to those attained from targets comprised of commonplace materials and to beam attenuations of less than 3 decades. Commonplace materials have effective atomic numbers in the range 5 to 26.

Since RDX has an effective atomic number of 7.16, composite thicknesses of RDX and iron will not cover the range 5 to 7.16 in effective atomic number unless (formally) negative thicknesses of iron are allowed. Use of (formally) negative thicknesses of iron overlay leads to computational difficulties. To overcome this problem, an additional set of $(M_H, M_L)$ points is generated using RDX as threat and boron as the overlay. With respect to a specific threat material, a boron overlay thickness can be corresponded with a iron overlay of (formally) negative thickness. For example, with respect to RDX, $-1$ gm/cm$^2$ of iron is (formally) equivalent to 114.7 gm/cm$^2$ of boron.

A final step in constructing a table of p-values is the selection of an appropriate grid of (H,L) values. Here an H or L value is the logarithmic high or low beam attenuation expressed in units employed by the machine's A-to-D converter. For example, with the current electronics, logarithmic attenuations output from the machine have a rescaling or conversion factor of 820 units per decade of attenuation. The current grid in HL space for which p-values are given is stratified into 100 rescaled attenuation values between 4 and 400, 75 between 408 and 1000 and 75 between 1016 and 2200. In computing p-values, attention may be restricted to those grid points realizable from material of effective atomic number between 5 and 26.

A particular grid point (H,L) is first rescaled to a corresponding point in logarithmic attenuation $(M_{HG}, M_{LG})$. This point will lie within a unique, smallest triangle of points obtained from the set previously generated by numerically varying threat and overlay thicknesses. The p-value for the grid point $(M_{HG}, M_{LG})$ is obtained by linear interpolation of the p-values from the containing triangle. As a final step, p-values are rounded off to the nearest integer and optionally offsets are added to eliminate (formally) negative p-values.

Luminance Dilation Technique for Filling in the Bomb Region

The substance detection algorithms detailed above only work along the edge of a substance to be detected. Since the backgrounds in bags are not uniform, only those pixels that are immediately across the edge of the suspect object will exhibit the shift in (H,L) values due to the bomb material alone. Pixels that are farther into or out of the bomb material will incorporate shifts in (H,L) values that are partially due to natural variations in the background, thus exhibiting a decrease in "hits" or "votes" as the algorithm moves farther from the bomb edge.

There are two reasons why we want to be able to fill in the center of a substance whose edge has been determined to appear to be a threat. The first reason is that we want to put up a clear signal to the operator of the system. A few red pixels on the edge of a substance may easily be missed by the operator.

The second reason for filling in the center is that this may be used as a part of an overall threat detection strategy. That is, we have to ring a bell when the likelihood of a threat exceeds some threshold. Some properties of the filled-in objects such as total area may aid in this determination.

The luminance dilation algorithm is one among several alternative algorithms whose goal is to extend threat pixels which have been detected along the edge of an object into the interior of objects.

The algorithm is performed locally inside of a box of a given size, centered on the pixel of interest. The dilation algorithm is repeated for each pixel in the image.

The algorithm is as follows. If there are more than some minimum number of threat pixels within the box (i.e. the number of red pixels), and if the K value of the pixel under consideration differs by less than some threshold from the average K value in the box, then mark this new pixel as a threat pixel. Note that K is now defined as the ratio of the high energy beam attenuation to the low energy beam attenuation for that single pixel.

If more than some number of pixels within the box are changed from non-threat pixels to threat pixels, then the algorithm backs up recursively by one half the box size so that the impact of the new threat pixels may be propagated to image regions which have already been done. The following parameters are tuning attributes of the algorithm which are determined empirically:

The size of the box within which the dilation is done.

The minimum number of threat pixels required for the box to be considered.

The maximum allowable difference in K values.

The number of changed pixels required to force a recalculation of earlier values.

For the experimental example given above, the size of the box is 11 pixels by 11 pixels, the minimum number of threat pixels is 8, and the maximum allowable difference in K values is 0.015.

Consider, as in FIGS. 9(a)–(c), a 4×4 box of pixels 600 overlying bomb material 690 with a number of threat pixels $N_{TREAT}$ greater than a minimum number $N_{MIN}$, the threat pixels 603, 606, 610, and 614 lying along an edge of bomb 690. Since the absolute value of the difference between the value $K_1$ for pixel 601 and the average value $K_{AV}$ for all pixels in box 600 is greater than the threshold value $\Delta K$, pixel 601 is left unchanged by the luminance dilation algorithm. However, because the absolute value of the difference between the value $K_7$ for pixel 607 and $K_{AV}$, and between the value $K_{12}$ for pixel 612 and $K_{AV}$, is less than or equal to $\Delta K$, pixels 607 and 612 have been newly marked in FIG. 9(b) as threat pixels. Similarly, in FIG. 9(c) the remaining new threat pixels have been marked.

Other Algorithmic Embodiments

An alternative preferred algorithmic embodiment employs comparisons between areas within the image that can be substantially larger than individual pixels. These areas are found by applying an edge finding algorithm, as described above, to the image data and filling in contiguous areas of edged objects in a manner substantially similar to the luminance dilation techniques described above. An advantage of such an areal comparison algorithm is a reduction in the statistical and quantum noise (roughly proportional to the square root of the number of x-ray quanta or photons in the x-ray beam) since typically many pixels are averaged over any given contiguous area within an edged object in the image.

Other Embodiments

A dual-energy x-ray inspection system to inspect for the presence of a specific substance, such as particular kinds of plastics, in the presence of unknown overlying materials such as plastic recycling plants where a particular form of plastic such as PVC or other halogenated hydrocarbon must be separated from other forms of plastic in shredded plastic refuse.

Additionally, a system could be developed that could detect the presence of "foreign" materials in foodstuffs, e.g. bones in boneless chicken, glass in chewing gum, etc.

A system could be developed that could inspect for minerals, e.g. diamonds, in the presence of a slurry or mixture of other rocks or materials.

A system to inspect for the presence of quantities of certain drugs in cargo or baggage could be developed.

A system to inspect for the presence of quantities of paper money in cargo or baggage could be developed.

X-ray Source Variations

The source could consist of a scanning x-ray pencil beam with a suitable (either scanning or line of detectors) detector.

The source could consist of a solid angle of x-rays of 2 energy bands with a suitable detector consisting of a 2-d matrix of detectors or films which are later analyzed.

The source could consist of an approximately or exactly mono-energetic x-ray source, obtained through appropriate filtering (K-edge) or a method such as x-ray lasers.

X-ray Detector Variations

The detector could consist of a line of PMT (photomultiplier tubes) coupled with scintillation materials.

The detector could consist of an array of proportional x-ray counters.

The detector could consist of 2 sheets of film, one for each band of x-rays, and the film later digitized and analyzed.

Conveyor Variations

The conveyor could consist of a series of interlocked or free wheeling rollers, either powered or gravity operated or some other form of material locomotion as in a manufacturing plant.

Baggage Detection Variations

The presence of baggage or other items to be inspected could be accomplished with acoustic means of detection at an appropriate sonic or supersonic frequency.

Computer Variations

The computer could consist of almost any suitable arrangement of a fast processor or processors with sufficient processing capacity to display the resulting image in a timely fashion. The performance required being strictly a function of practical requirements external to the demands of the algorithm.

The host could be any commercial or custom processor and peripheral circuits.

The detection computing means could be done by the host or by a separate or embedded array processor or arrays of computing elements.

Display Variations

The display could be any form of computer display device such as color TV monitor, LCD display screen, or plasma flat panel. Such a display device may be black and white and scales of grey, or some other monochrome variation (with highlighted pixels flashing or otherwise indicated), or color with various choices of resolution.

Operator Console Variations

The operator's console could be replaced with an interface to a factory management computer network, which would issue the correct commands and utilize the image or other data output by the inspection machine.

The operator console could be activated by use of another computer screen located on a computer connected to the inspection system via a computer network or other communication port. This remote console could also display the image available from the inspection system with additional image and threat processing software available.

Calibration Algorithm Variations

The dark current and air point compensation algorithm could be recast in a new form to be more computationally amenable in real time. For example this algorithm could be done equivalently as:

$$H = k(\text{Log}_{10}[\chi_{AirH} - \chi_{Dark}] - \text{Log}_{10}[\chi_{SampleH} - \chi_{Dark}])$$

$$L = k(\text{Log}_{10}[\chi_{AirL} - \chi_{Dark}] - \text{Log}_{10}[\chi_{SampleL} - \chi_{Dark}]).$$

Heuristic-Like Techniques

When inspecting for specific known objects, information regarding characteristics of the specific object such as their known shape, texture, or thickness can be employed to formulate respective heuristic-like techniques for improving the accuracy of the determinations.

Dual Energy X-Ray Inspector and Computed Tomography

A dual energy x-ray inspection device 1000 can be used in conjunction with a computed tomographic (CT) scanner 1002 (also known as a computerized axial tomographic or CAT scanner), as illustrated in FIGS. 18a and 18b. The CT scanner 1002 provides information relevant to the three dimensional spatial configurations of objects within the baggage, for example, such as thicknesses of overlying materials, but takes a relatively long time to process each CT scan and so is not suitable to be solely responsible for detecting and indicating suspect specific materials on-line in real time. Coupling a CT scanner 1002 with a dual energy x-ray inspection device 1000, as shown schematically in FIG. 18a, increases the algorithmic efficiency of the baggage inspection, the dual energy x-ray device 1000 serving to indicate suspect slices in the baggage that warrant further, more detailed, inspection by the CT scanner 1002, which is not employed otherwise. Positional information concerning the locations of the suspicious regions are conveyed from the dual energy x-ray inspector 1000 to the CT scanner 1002. Alternatively, as shown in FIG. 18b, the x-ray source and detectors in the dual energy x-ray inspector device 1004 can be deployed to also perform CT scanning when required. In such embodiments 1004, a somewhat less accurate dual energy x-ray system can be tolerated, for example one using coarser grained pixels, because of the additional CT scanning capabilities.

Other embodiments are within scope of the following claims.

An appendix is attached.

APPENDIX TO
DEVICE AND METHOD FOR INSPECTION
OF BAGGAGE AND OTHER OBJECTS

ALGO.DOC                    Thursday, May 3, 1990 9:12 am

```
#define MIN_HI      1
#define MAX_HI      2001
define HI_INDEX    1 define MAX_IDX 4000

/* #define TISSUE */       /* Tissue-equivalent epoxy plastic */
#define C4                 /* C4 plastic explosive */
/* #define RDX */          /* RDX sheet explosive */
/* #define WG */           /* Water Gel explosive */
/* #define DYN */          /* 40% dynamite stick */

/* new way of determining low */
#define z1 .0247
#define z2 .01492
#define z3 .265
#define z4 112.6
#define z5 25.198
#define z6 .6218
#define z7 .265

/* define substance parameters */ ifdef WG
define c1 9.732
#define c2 6.108
#define c5 1.218
#define K0 .547
#define KL .961
endif ifdef RDX
define c1 9.732
#define c2 6.108
#define c5 1.218
#define K0 .65
#define KL .86
endif ifdef C4
define c1 9.732
#define c2 6.108
#define c5 1.218
#define K0 .6522
#define KL .87
endif ifdef DYN
define c1 570.46
#define c2 4.352
#define c5 .304
```

```
#define K0 .522
#define KL .765
endif ifdef TISSUE
define c1 3798
#define c2 3.8837
#define c5 0.993
#define K0 .655
#define KL .825
endif double bh(double km);
double bh(double km)
{
    return(c1*pow((km+c5),c2));
} double Kref(double Hi,double Km,double k0);
double Kref(double Hi,double Km,double k0)
{ return (((Hi+bh(Km))*k0*KL)/((bh(Km)*KL)+(Hi*k0)));
} double alpha(double km);
double alpha(double km)
{
    return((z1+(z2*km)-(z2*z3))/(km*km));
}
double beta(double km);
double beta(double km)
{
    return((z4+((z6-km)*(z5/(z6-z7))))/km);
} double newlow(double h,double km);
double newlow(double h,double km)
{
    return (h*(1/(km+(alpha(km)*(h/(h+beta(km)))))));

} double find_Km(double hi,double Kair,double kref);
double find_Km(double hi,double Kair,double kref)
{
    /* find the Km that approximates the desired Kref given high val,k0 */
    int x,bitval;
    double lsbval,approx_kref;
```

```c
    lsbval = 0.8;
    bitval = 0;

for (x=0;x<8;x++)
    {
        bitval=(bitval<<1)|1;
        lsbval = lsbval/(double)2.0;

approx_kref = (Kref(hi,((double).1+((double)bitval*lsbval)),Kair));

if (approx_kref < kref)
            bitval=bitval&(0xfe) ;

}
    return (((double)bitval*lsbval)+.1);
}
double findKm_Low(double hi,double low);
double findKm_Low(double hi,double low)
{
    /* find the Km that approximates the desired Low given high val,k0 */
    int x,bitval;
    double lsbval,approx_low;

lsbval = 0.8;
    bitval = 0;

for (x=0;x<8;x++)
    {
        bitval=(bitval<<1)|1;
        lsbval = lsbval/(double)2.0;

approx_low = (Low(hi,((double).1+((double)bitval*lsbval))));

if (approx_low < low)
            bitval=bitval&(0xfe) ;

}
    return (((double)bitval*lsbval)+.1);
}

/* create the histogram */
    for (hint = MIN_HI; hint < MAX_HI; hint += HI_INDEX)
    {
        h = (double)hint;                          /* Get hi double value */

/* Set up the header values and the KIdx */
        Hdr[HI_VALUE] = hint;
        KIdx = 0;
```

```c
/* Get the hi and lo kref */
hi_kref = Kref(h, 0.29, k0);
lo_kref = Kref(h, 0.8, k0);
k=lo_kref;

lastl = -100.0;
diffl = 1000.0;
while (k<hi_kref)
{
    km=find_Km(h,k0,k);
    kr=Kref(h,km,k0);
    l=Low(h,km);
    if (((l-lastl)<diffl)&&(km>.29))
        diffl = l - lastl;

lastl = l;

if (h>800.0)
    {
        k=k*1.04;
    } else
        k=1.01*k;        /* 1% bins */

}

/* do it again, but use diffl to find values */
k=lo_kref;
km=find_Km(h,k0,k);
l=Low(h,km);
findl=(int)l;

/* adjust diffl to a power of 2 */
tdiffl=0;
while ((1 << (tdiffl+1)) <= (int)diffl)
    tdiffl++;

km=findKm_Low(h,(double)findl);
k=Kref(h,km,k0);

/* Save the minimum low and the scale factor */
Hdr[MIN_LO] = findl;
Hdr[LO_SCALE] = tdiffl;

while (k < hi_kref)
{
    km=findKm_Low(h,(double)findl);
    k=Kref(h,km,k0);

/* Save the necessary information into the values */
    KrefTab[KIdx] = (float)k;
```

```
            KIdx++;

/* increment low */
            findl += (1 << tdiffl);

/* increment bin count */
            bincnt+=1;

}

/* Now we have the table, write out the header then the table */
        Hdr[MAX_LO] = findl;
        bwritten = write (fhndl, (char *)Hdr, sizeof(int)*4);
        if (bwritten != (sizeof(int) * 4))
        {
            printf("Error writing file\n");
            return(1);
        }

/* Now write out the kref vector */
        bwritten = write (fhndl, (char *)KrefTab, sizeof(float)*KIdx);
        if (bwritten != (sizeof(float)*KIdx))
        {
            printf("Error writing file\n");
            return(1);
        }
    }

/* output bin count */
    printf("Total Kref bin count :%ld\n",bincnt);
```

```
/*
        Detection algorithm for above histogram
*/
/*
 * Function:
 *      DoBox
 *
 * Descrition:
 *      Process the box.
 *
 * Usage:
 *      DoBox (x, y)
 *
 * Inputs:
 *      x - int : the x coordinate of the candidate pixel
 *      y - int : the y coordinate of the candidate pixel
 *
```

```
 * Outputs:
 *      None
 */
static void DoBox (int x, int y)
{
    int tx, ty;
    double diffH, diffL, diffK;
    double kreflo,krefhi,krefavg;
    /* int tmp; */
    double mindiff;
    Pixel *midpxl = &ScanLine[y][x];
    Pixel *pxl;

/* Average the values for this pixel */
    AveragePixel (x, y);

/* See if we need to do this pixel */
    if (midpxl->avghia > 2000.0)
        return;

/*
     * Calculate the min difference value (this is calculated by using
     * twice the expected noise as the difference value).
     */
    mindiff = (10000.0/(100.0+midpxl->avghia));

/* Now loop through the pixels doing the box */
    for (ty = y - BORDER; ty <= (y + BORDER); ty++)
    {
        /* Get the pixel */
        pxl = &ScanLine[ty][x - BORDER];

/* Loop through the x */
        for (tx = x - BORDER; tx <= (x + BORDER); tx++, pxl++)
        {
            /* See if we need to look at this pixel (edges are no-nos) */
            if (pxl->sobel)
                continue;

/* Average this sucker */
            AveragePixel (tx, ty);

/* Now difference the Hi AIRS */
            diffH = midpxl->avghia - pxl->avghia;

/* Now threshold it */
            if (diffH < mindiff)
                continue;

/* Now difference the Lo AIRS */
            diffL = midpxl->avgloa - pxl->avgloa;
```

```
            /* Now threshold it */
            if ((diffL < mindiff) || (diffL == 0.0))
                continue;

kreflo=LookupKref(pxl->avghia,pxl->avgloa);
            krefhi=LookupKref(midpxl->avghia,midpxl->avgloa);

diffK = diffH/diffL;

/* Key lookup algorithm
             * Histogram generation algorithm has been fit to this ratio
             */ krefavg=(kreflo*.8)+(.2*krefhi);

/* See if we need to histogram this point */
            if ((diffK < (krefavg+(MinThreshold)))
                || (diffK >(krefavg+(MaxThreshold))))
                continue;

midpxl->histval++;
        }
    } if (maxhit<midpxl->histval)
        maxhit=midpxl->histval;
    if(midpxl->histval > fomThresh)
        fom += (midpxl->histval - fomThresh);

if ((midpxl->histval > 0) && (midpxl->histval <200))
        histpix[midpxl->histval]++;

}
```

We claim:

1. A method of detecting a target object of a specific material of interest in a continuously moving ensemble of initially unidentified objects, comprising:

providing a stationary X-ray exposure system, a stationary X-ray detection system, and a computer operatively connected to said detection system, continuously moving said ensemble of objects on a conveyor through an inspection station, at said inspection station, progressively exposing said initially unidentified ensemble of objects to X-ray radiation by continuous movement of said ensemble through a beam produced by said stationary X-ray exposure system.

detecting the X-ray radiation transmitted through said ensemble of objects with said stationary X-ray detection system, and providing to said computer X-ray data corresponding to the intensity of transmitted radiation, over the area of the thus-exposed ensemble, calculating a value characteristic of said target object of said specific material of interest in said ensemble of objects, and therewith identifying said target object, systematically utilizing in said calculations X-ray transmission data of rays from said stationary X-ray exposure system passing through said ensemble of objects, including rays passing through said target object of said specific material of interest as well as rays passing near but not through said target object to remove the contribution of overlying and underlying material from the calculated value characteristic of said target object of said specific material of interest, and automatically indicating the presence of said target object while said ensemble of objects progresses on said conveyor, and wherein the calculating step further includes choosing at least one target region and successively examining a plurality of regions in the neighborhood of said at least one target region.

2. The method of claim 1 wherein X-ray data from rays that pass through different regions of said target object of said specific material of interest are employed in said calculations in a manner that selectively averages many pixels over contiguous regions reduce noise in calculating said value.

3. The method of claim 1 herein said stationary x-ray exposure system exposes said ensemble to at least one fan beam of x-ray radiation to produce said x-ray data.

4. The method of claim 1 wherein said ensemble is exposed to x-ray radiation at more than one energy to produce said x-ray data and the resulting data at more than one energy is used in calculating said value characteristic of said target object of said specific material of interest.

5. The method of claim 4 wherein said x-ray radiation at each energy is of fan beam form.

6. The method of claim 4 wherein said x-ray exposure system emits alternately pulses of x-ray radiation of two substantially different x-ray energies.

7. The method of claim 4 wherein said x-ray exposure system includes at least one x-ray source that emits polychromatic x-ray radiation, and said x-ray detection system includes two sets of x-ray detectors that detect x-ray radiation of respectively different x-ray energies.

8. The method of claim 2, or 4 wherein said ensemble comprises an article of luggage or package and its contents and said step of exposing comprises employing at least one fan beam of x-ray radiation emanating from said x-ray exposure system and moving the article on a conveyor past said at least one fan beam.

9. The method of claim 8 wherein the transmitted fan beam of x-ray radiation is detected by at least one linear array of detectors of said x-ray detection system.

10. The method of claim 1 or 4 wherein said value that is characteristic of said target object relates directly to a physical characteristic of the specific material of said target object.

11. The method of claim 10 wherein said physical characteristic is the atomic number Z.

12. The method of claim 1 or 4 wherein said target object of said specific material of interest is one of the following: plastic explosives, other explosives, drugs and money.

13. The method of claim 1 or 4 employed to detect plastic explosive objects in packages or luggage which contain harmless objects having Z values of plastics different from said plastic explosive.

14. The method of claim 1 wherein said exposure system and said detection system produce dual image information of said ensemble and said computer processes the resultant dual image information to detect said specific material on the basis of comparisons of selected subareas of the exposed area of said ensemble to other subareas thereof in the vicinity of the selected subareas.

15. The method of claim 14 wherein said exposure system and said detection system produce said dual image information in the form of dual energy information.

16. The method of claim 14 employed to detect a bomb that may be present in said ensemble.

17. The method of claim 1,2 or 4 used in conjunction with CT scanning of said ensemble.

18. The method of claim 17 employed to produce information relevant to three dimensional spatial configurations of objects within said ensemble.

19. The method of claim 17 used in conjunction with a separate CT scanner.

20. The method of claim 17 which said x-ray exposure system and said x-ray detection system are deployed to also perform CT scanning.

21. The method of claim 1,2 or 4 used as a preliminary scan to inspect articles of luggage and packages online substantially in real time, and CT scanning is thereafter performed on suspect regions of said articles as determined by said preliminary scan.

22. The method of claim 1,2 or 4 used to indicate suspect slices in articles of luggage and packages, followed by CT scanning of said suspect slices.

23. The method of claim 1,2 or 4 wherein said computer is programmed to automatically indicate presence and location of said target object on a video display.

24. The method of claim 1,2 or 4 wherein said computer is programmed to determine an image of said target object by first identifying a region exhibiting said value that is characteristic of said target object and then employing a dilation algorithm upon said x-ray data to determine nearby regions that have similar values.

25. The method of claim 24 wherein the determined image of said target object is displayed on a video display.

26. The method of claim 24 wherein presence of said target object is indicated by an alarm.

27. The method of claim 24 wherein said computer is further programmed to reduce noise of the predetermined image by applying an erosion algorithm.

28. The method of claim 27 wherein the resultant noise-reduced image is displayed on a video display.

29. The method of claim 1,2 or 4 wherein said computer employs, for reference information, a predetermined lookup table based on actual measurements performed on said specific material of interest under varying conditions.

30. The method of claim 29 wherein said varying conditions comprise variations in thickness of said specific material of interest.

31. The method of claim 1,2 or 4 wherein said calculating includes calculating values substantially related to the logarithm of the energy of rays transmitted through the target object of the specific material of interest and of rays transmitted not through the target object but through regions adjacent to the target object and then subtracting from the resultant target values part or all of the resultant adjacent region values.

32. The method of claim 1,2 or 4 wherein said x-ray exposure system produces timed emissions of x-ray pulses and said x-ray detection system and said computer operate co-operatively so that said detection system collects x-ray data during emission of said x-ray pulses and said detection system collects "no x-ray flux" data between pulses when no x-rays are emitted from said x-ray exposure system, said computer further programmed to receive both said x-ray data and said "no x-ray flux" data from said detection system and to correct said x-ray data by equalizing said x-ray data with said "no x-ray flux" data.

33. The method of claim 1,2 or 4 wherein the step of identifying said target object employs evaluation of the magnitude of the gradient of the calculated values over the area of the ensemble that has been exposed to said x-ray radiation.

34. A device for detecting a target object of a specific material of interest in a continuously moving ensemble of initially unidentified objects, comprising a conveyor arranged to move said ensemble of objects continuously through an inspection station, a stationary X-ray exposure system and a stationary X-ray detection system both constructed to operate cooperatively with said conveyor, and a computer operatively connected to said detection system, said stationary X-ray exposure system constructed and positioned to progressively expose, at said inspection station, said ensemble of initially unidentified objects to X-ray radiation by continuous movement of said ensemble through a beam produced by said X-ray-exposure system, said stationary X-ray detection system positioned to detect X-ray radiation transmitted through said ensemble of objects, and constructed to provide to said computer X-ray data corresponding to the intensity of transmitted radiation, said computer programmed to calculate, over the area of the thus-exposed ensemble, a value characteristic of said target object of said specific material of interest in said ensemble of objects, and therewith identifying said target object, said computer programmed to systematically utilize in said calculations X-ray transmission data of rays from said stationary X-ray exposure system passing through said ensemble of objects, including rays passing through said target object of said specific material of interest as well as rays passing near but not through said target object to remove the contribution of overlying and underlying material from the calculated value characteristic of said target object of said specific material, said computer programmed so that the removal of the contribution of overlying and underlying material from said calculated value is dependent upon determining an edge of the target object, and said computer programmed to indicate the presence of said target object.

35. The device of claim 34 wherein said computer is programmed to employ x-ray data from rays that pass through different regions of said target object of said specific material of interest in performing said calculation.

36. The device of claim 34 wherein said stationary x-ray exposure system is constructed to expose said ensemble to at least one fan beam of x-ray radiation to produce said x-ray data.

37. The device of claim 34 wherein said x-ray exposure system is constructed to expose said ensemble to x-ray radiation at more than one energy to produce said x-ray data and the computer is programmed to employ resulting data at more than one energy is used in calculating said value characteristic of said target object of said specific material of interest.

38. The device of claim 37 wherein said x-ray exposure system is constructed to produce said x-ray radiation at each energy in fan beam form.

39. The device of claim 37 wherein said physical characteristic is the atomic number Z.

40. The device of claim 34, 37 or 38 constructed to receive said ensemble in the form of an article of luggage or package and said exposure system directs at least one fan beam of x-ray radiation through said article of luggage or package as the article moves past said at least one fan beam.

41. The device of claim 40 wherein said detection system is arranged to detect the transmitted fan beam of x-ray radiation with at least one linear array of detectors.

42. The device of claim 34 or 37 wherein said value that is characteristic of said target object is selected to relate directly to a physical characteristic of the specific material of said target object.

43. The device of claim 34 or 37 wherein said target object of said specific material of interest is one of the following: plastic explosives, other explosives, drugs and money.

44. The device of claim 34 or 37 programmed to detect plastic explosive objects in packages or luggage which contain harmless objects having Z values of plastics different from said plastic explosive.

45. The device of claim 34 wherein said exposure system and said detection system are constructed to produce dual image information of said ensemble and said computer is programmed to process the resultant dual image information to detect said specific material on the basis of comparisons of selected subareas of the exposed area of said ensemble to other subareas thereof in the vicinity of the selected subareas.

46. The device of claim 45 wherein said exposure system and said detection system produce said dual image information in the form of dual energy information.

47. The device of claim 45 programmed to detect a bomb that may be present in said ensemble.

48. The device of claim 34 or 37 combination with means for CT scanning of said ensemble.

49. The combination of claim 48 constructed and arranged to produce information relevant to three dimensional spatial configurations of objects within said ensemble.

50. The combination of claim 48 having a CT scanner separate from said device.

51. The combination of claim 48 in which said x-ray exposure system and said x-ray detection system of said device are deployed to also perform CT scanning.

52. A system including the device of claim 34 or 37 and CT scanning means, said device constructed and arranged for use as a preliminary scan to inspect articles of luggage and packages on-line substantially in real time, and said CT scanning means arranged thereafter to inspect suspect regions of said articles as determined by said preliminary scan.

53. A system including the device of claim 34 or 37 constructed and arranged to indicate suspect slices in articles of luggage and packages and CT scanning means arranged to scan said suspect slices.

54. The device of claim 34 or 37 wherein said computer is programmed to automatically indicate presence and location of said target object on a video display.

55. The device of claim 34 or 37 wherein said computer is programmed to determine an image of said target object by first identifying a region exhibiting said value that is characteristic of said target object and then employing a dilation algorithm upon said x-ray data to determine nearby regions that have similar values.

56. The device of claim 55 constructed to display the determined image of said target object on a video display.

57. The device of claim 55 constructed to indicate presence of said target object is indicated by an alarm.

58. The device of claim 55 wherein said computer is further programmed to reduce noise of the predetermined image by applying an erosion algorithm.

59. The device of claim 58 constructed and arranged to display the resultant noise-reduced image is displayed on a video display.

60. The device of claim 34 or 37 wherein said computer is programmed to employ, for reference information, a predetermined lookup table based on actual measurements performed on said specific material of interest under varying conditions.

61. The device of claim 60 wherein said varying conditions comprise variations in thickness of said specific material of interest.

62. The device of claim 34 or 37 wherein said computer is programmed to calculate values substantially related to the logarithm of the energy of rays transmitted through the target object of the specific material of interest and of rays transmitted not through the target object but through regions adjacent to the target object and then subtracting from the resultant target values part or all of the resultant adjacent region values.

63. The device of claim 34 wherein said x-ray exposure system is constructed to emit alternately pulses of x-ray radiation of two substantially different x-ray energies.

64. The device of claim 34 wherein said x-ray exposure system includes at least one x-ray source that emits polychromatic x-ray radiation, and said x-ray detection system includes two sets of x-ray detectors that detect x-ray radiation of respectively different x-ray energies.

65. The device of claim 34 or 37 wherein said x-ray exposure system is constructed to produce timed emissions of x-ray pulses and said x-ray detection system and said computer arranged to operate co-operatively so that said detection system collects x-ray data during emission of said x-ray pulses and said detection system collects "no x-ray flux" data between pulses when no x-rays are emitted from said x-ray exposure system, said computer further programmed to receive both said x-ray data and said "no x-ray flux" data from said detection system and to correct said x-ray data by equalizing said X-ray data with said "no x-ray flux" data.

66. The device of claim 34 or 37 wherein said computer is programmed to identify said target object by evaluation of the magnitude of the gradient of the calculated values over the area of the ensemble that has been exposed to said x-ray radiation.

67. The device of claim 34 or 37 including an interface of said computer with a computer network that utilizes the indications produced by said device.

68. For detection of a threat object, the device of claim 34 or 37 combination with a second computer programmed to utilize the indications from said device and additional threat processing software.

69. A baggage inspection system including the device of claim 34 or 37 and a further apparatus constructed to respond to indications from said device to facilitate a further inspection.

70. The inspection system of claim 69 wherein said further apparatus is a CT scanner.

71. A method of detecting a target object of a specific material of interest in a continuously moving article of luggage or package the contents of which are initially unidentified, comprising:

providing a stationary X-ray exposure system capable of producing at least one fan beam of X-ray radiation, a stationary X-ray detection system capable of detecting fan beam radiation, and a computer operatively connected to said detection system, continuously moving said ensemble of objects on a conveyor through an inspection station, at said inspection station, progressively exposing said article of luggage or package to x-ray radiation by continuous movement of said article of luggage or package through said fan beam produced by said stationary X-ray exposure system, detecting the X-ray radiation transmitted through said article of luggage or package with said stationary X-ray detection system, and providing to said computer X-ray data corresponding to the intensity of transmitted radiation, over the area of the thus-exposed article of luggage or package, calculating values characteristic of said target object of said specific material of interest in said luggage or package and therewith identifying said target object, systematically utilizing in said calculations X-ray transmission data of rays from said stationary x-ray exposure system passing through said article of luggage or package, including rays passing through said target object of said specific material of interest as well as rays passing near but not through said target object to remove the contribution of overlying and underlying material from the calculated value characteristic of said target object of said specific material of interest, the removal of the contribution of overlying and underlying material from said calculated value being dependent upon determining an edge of the target object, and automatically indicating the presence of said target object while said article of luggage or package progresses on said conveyor.

72. The method of claim 71 wherein X-ray data from rays that pass through different regions of said target object of said specific material of interest are employed in said calculations a manner that effectively averages many pixels over contiguous regions to reduce noise in calculating said value.

73. The method of claim 71 wherein said article of luggage or package is exposed to X-ray radiation at more than one energy to produce said X-ray data and the resulting data at more than one energy is used in calculating said value characteristic of said target object of said specific material of interest.

* * * * *